United States Patent
Heaton, II et al.

(10) Patent No.: US 11,457,844 B1
(45) Date of Patent: Oct. 4, 2022

(54) USING AN OXIMETER PROBE TO DETECT INTESTINAL ISCHEMIA

(71) Applicant: ViOptix, Inc., Newark, CA (US)

(72) Inventors: Larry C. Heaton, II, Pleasanton, CA (US); Robert E. Lash, Redwood City, CA (US); Jimmy Jian-min Mao, Fremont, CA (US)

(73) Assignee: ViOptix, Inc., Newark, CA (US)

( * ) Notice: Subject to any disclaimer, the term of this patent is extended or adjusted under 35 U.S.C. 154(b) by 521 days.

(21) Appl. No.: 16/502,010

(22) Filed: Jul. 2, 2019

Related U.S. Application Data

(62) Division of application No. 15/223,788, filed on Jul. 29, 2016, now Pat. No. 10,335,070, which is a
(Continued)

(51) Int. Cl.
*A61B 5/00* (2006.01)
*A61B 5/1455* (2006.01)
(Continued)

(52) U.S. Cl.
CPC .......... *A61B 5/14551* (2013.01); *A61B 1/018* (2013.01); *A61B 1/0638* (2013.01); *A61B 1/31* (2013.01); *A61B 5/0024* (2013.01); *A61B 5/14503* (2013.01); *A61B 5/14552* (2013.01); *A61B 5/4255* (2013.01); *A61B 5/6848* (2013.01); *A61B 5/6852* (2013.01); *A61B 5/7282* (2013.01); *A61B 5/742* (2013.01); *A61B 17/122* (2013.01); *A61B 5/0095* (2013.01);
(Continued)

(58) Field of Classification Search
CPC ... A61B 5/14551; A61B 1/018; A61B 1/0638; A61B 1/31; A61B 5/0024; A61B 5/14503; A61B 5/14552; A61B 5/4255; A61B 5/6848; A61B 5/6852; A61B 5/7282; A61B 5/742; A61B 17/122; A61B 5/0095; A61B 5/1455; A61B 2017/12004; A61B 2505/05; A61B 2560/0223; A61B 2562/0233
USPC ....................................................... 600/339
See application file for complete search history.

(56) References Cited

U.S. PATENT DOCUMENTS 2,198,319 A   10/1938   Silverman
4,609,370 A    9/1986   Morrison
(Continued)

OTHER PUBLICATIONS

Benaron, David et al., "Design of a Visibile-Light Spectroscopy Clinical Tissue Oximeter", Journal of Biomedical Optics, vol. 10/4, Jul./Aug. 2005, pp. 044005-1-044005-9.
(Continued)

*Primary Examiner* — May A Abouelela
(74) *Attorney, Agent, or Firm* — Aka Chan LLP

(57) ABSTRACT

Devices and systems have a sensor probe configured to measure tissue oxygen saturation in the intestine or mesentery. The devices and systems can determine the oxygenation state of the entire thickness of the intestine or mesentery. Embodiments of the invention also include methods for inducing a temporary ischemic period in an intestine or mesentery tissue and analyzing changes in oxygen saturation of the tissue during the temporary ischemic period or during a recovery phase. The devices, systems, and methods can be applied in diagnosing intestinal ischemia in a patient, as well as in monitoring tissue oxygen saturation of the intestine or mesentery during or after a surgical procedure.

22 Claims, 17 Drawing Sheets

Related U.S. Application Data division of application No. 12/410,155, filed on Mar. 24, 2009, now Pat. No. 9,737,213.

(51) Int. Cl.
| | |
|---|---|
| *A61B 17/122* | (2006.01) |
| *A61B 5/145* | (2006.01) |
| *A61B 1/06* | (2006.01) |
| *A61B 1/018* | (2006.01) |
| *A61B 1/31* | (2006.01) |
| *A61B 17/12* | (2006.01) |

(52) U.S. Cl.
CPC ... *A61B 5/1455* (2013.01); *A61B 2017/12004* (2013.01); *A61B 2505/05* (2013.01); *A61B 2560/0223* (2013.01); *A61B 2562/0233* (2013.01)

(56) References Cited

U.S. PATENT DOCUMENTS

| | | | | |
|---|---|---|---|---|
| 4,785,814 | A * | 11/1988 | Kane | A61B 5/14539 356/41 |
| 4,890,619 | A | 1/1990 | Hatschek | |
| 4,947,850 | A * | 8/1990 | Vanderkooi | A61B 5/0059 600/431 |
| 5,012,809 | A | 5/1991 | Shulz | |
| 5,299,570 | A | 4/1994 | Hatschek | |
| 5,357,954 | A * | 10/1994 | Shigezawa | A61B 5/1459 600/339 |
| 5,593,899 | A * | 1/1997 | Wilson | A61B 5/0059 422/79 |
| 5,673,694 | A * | 10/1997 | Rivers | A61B 5/1459 356/41 |
| 5,782,804 | A * | 7/1998 | McMahon | A61M 5/3234 604/110 |
| RE36,434 | E | 12/1999 | Hamlin et al. | |
| 6,078,833 | A | 6/2000 | Hueber | |
| 6,167,297 | A * | 12/2000 | Benaron | A61B 5/0071 600/431 |
| 6,277,082 | B1 | 8/2001 | Gambale | |
| 6,280,701 | B1 | 8/2001 | Carter et al. | |
| 6,306,908 | B1 * | 10/2001 | Carlson | A61K 31/202 514/560 |
| 6,498,942 | B1 | 12/2002 | Esenaliev et al. | |
| 6,516,209 | B2 * | 2/2003 | Cheng | A61B 5/14546 250/252.1 |
| 6,587,703 | B2 * | 7/2003 | Cheng | A61B 5/14546 600/310 |
| 6,597,931 | B1 | 7/2003 | Cheng et al. | |
| 6,711,426 | B2 * | 3/2004 | Benaron | A61B 5/0075 600/342 |
| 6,735,458 | B2 | 5/2004 | Cheng et al. | |
| 6,801,648 | B2 | 10/2004 | Cheng | |
| 7,043,287 | B1 * | 5/2006 | Khalil | A61B 5/0059 600/310 |
| 7,120,481 | B2 * | 10/2006 | Keller | A61B 5/0261 600/339 |
| 7,247,142 | B1 * | 7/2007 | Elmandjra | A61B 5/02007 600/323 |
| 7,331,943 | B2 | 2/2008 | Mascitelli et al. | |
| 7,355,688 | B2 | 4/2008 | Lash et al. | |
| 7,469,158 | B2 * | 12/2008 | Cutler | A61B 5/14542 600/325 |
| 7,758,505 | B2 | 7/2010 | Fine et al. | |
| 7,831,298 | B1 * | 11/2010 | Wang | A61B 18/1815 600/473 |
| 9,339,221 | B1 * | 5/2016 | Heaton, II | A61B 5/6852 |
| 2003/0236452 | A1 | 12/2003 | Melker et al. | |
| 2004/0039274 | A1 * | 2/2004 | Benaron | G01J 3/10 600/342 |
| 2004/0152187 | A1 * | 8/2004 | Haight | C12Q 1/54 435/287.1 |
| 2004/0247268 | A1 | 12/2004 | Ishihara et al. | |
| 2005/0113719 | A1 * | 5/2005 | Saadat | A61B 5/14542 600/585 |
| 2005/0177035 | A1 * | 8/2005 | Botvinick | A61B 5/1495 600/347 |
| 2006/0100595 | A1 * | 5/2006 | von Dyck | A61B 5/14539 604/348 |
| 2006/0200012 | A1 * | 9/2006 | Mansour | A61B 5/14539 600/310 |
| 2006/0224053 | A1 * | 10/2006 | Black | A61B 5/413 600/310 |
| 2007/0027371 | A1 * | 2/2007 | Benaron | A61B 5/0031 600/310 |
| 2007/0038126 | A1 * | 2/2007 | Pyle | A61B 5/0084 600/476 |
| 2007/0197888 | A1 * | 8/2007 | Axelrod | A61B 5/14542 600/339 |
| 2008/0027300 | A1 * | 1/2008 | Barclay | A61B 5/14542 600/339 |
| 2008/0106792 | A1 | 5/2008 | Lash et al. | |
| 2008/0108886 | A1 | 5/2008 | Lash et al. | |
| 2008/0319290 | A1 | 12/2008 | Mao et al. | |
| 2009/0054908 | A1 * | 2/2009 | Zand | A61B 34/30 606/130 |
| 2009/0156932 | A1 * | 6/2009 | Zharov | G01N 21/39 600/437 |
| 2009/0216097 | A1 | 8/2009 | Wilson et al. | |
| 2009/0292187 | A1 * | 11/2009 | Mao | A61B 17/025 600/339 |
| 2010/0036209 | A1 | 2/2010 | Ferren et al. | |
| 2010/0191081 | A1 * | 7/2010 | Shahidi | A61B 5/14555 600/323 |
| 2012/0136225 | A1 * | 5/2012 | Benni | A61B 5/14551 600/323 |
| 2012/0289801 | A1 * | 11/2012 | Yamaguchi | A61B 1/00009 600/328 |
| 2015/0282694 | A1 * | 10/2015 | Morimoto | A61B 1/0638 600/339 |

OTHER PUBLICATIONS

Hirano, Yasumitso et al., "Near-Infrared Spectroscopy for Assessment of Tissue Oxygen Saturation of Transplanted Jejunal Autografts in Cervical Esophageal Reconstruction", Surgery Today, 2005, vol. 35, pp. 67-72.

"Intraoperative Assessment of Microperfusion with Visible Light Spectroscopy in Colorectal Anastomosis", Diagnostic Optical Spectroscopy in Biomedicine IV, Proc. of SPIE-OSA, vol. 6628, 2007, pp. 662816-1-662816-8.

Musgrove, Cameron et al., "Computational Aspects of Endoscopic (Trans-rectal) Near-infrared Optical Tomography: Initial Investigations", Optical Tomography and Spectroscopy of Tissue VII, Proc. of SPIE, vol. 6434, 2007, pp. 643409-1-643409-10.

Rosenthal, Lawrence et al., "Internal Ischemia", http://www.gi.org/patients/gihealth/ischemia.asp, American College of Gastroenterology, 2006, 3 pages, (viewed Mar. 10, 2009).

Williams, Julian, "Encoscope and Laser Treatment", http://julzwilliams.com/files/physics/ endolaser/partsofendoscope.html, 2008, 1 page, (viewed Mar. 10, 2009).

\* cited by examiner

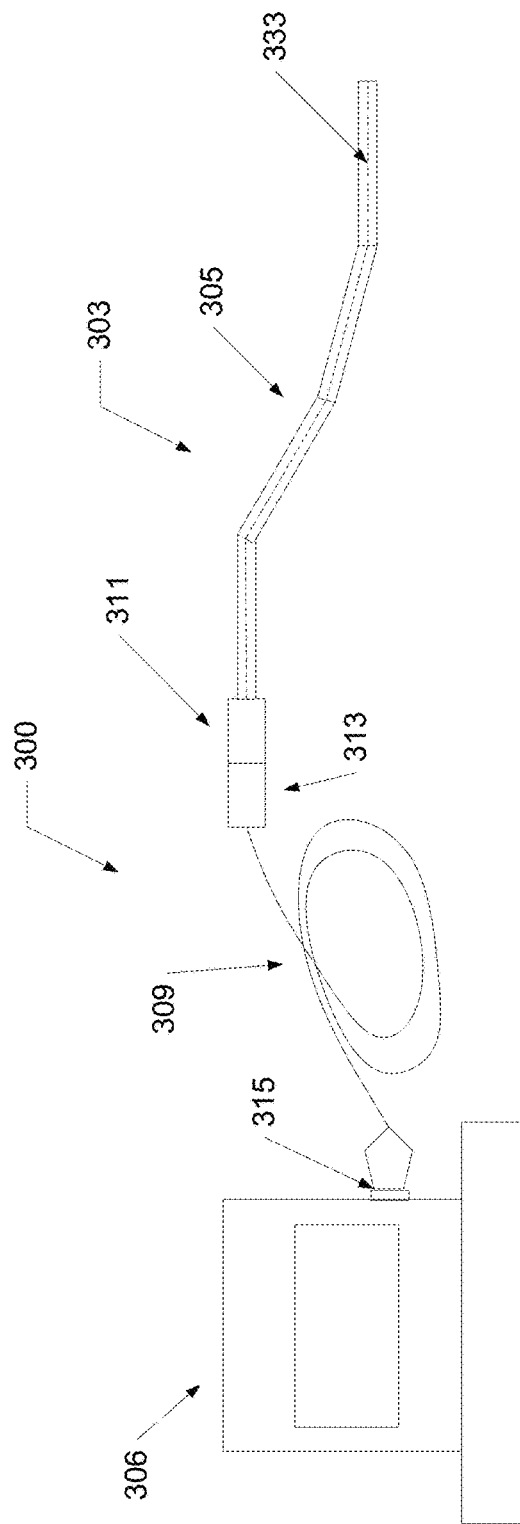
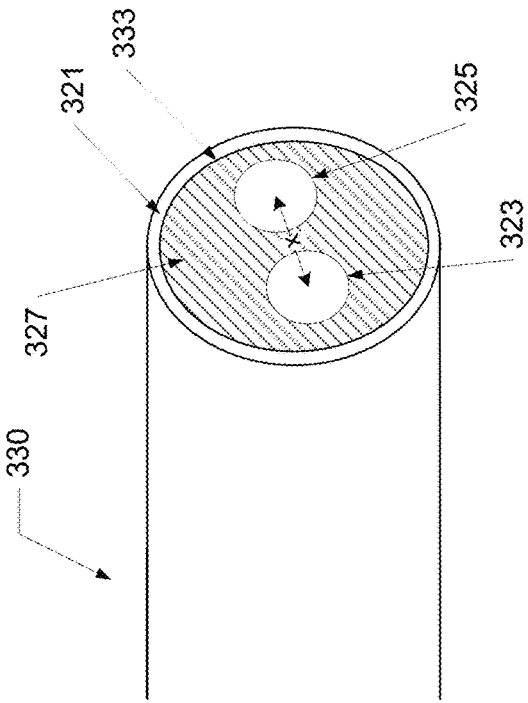
Figure 3A
Figure 3B

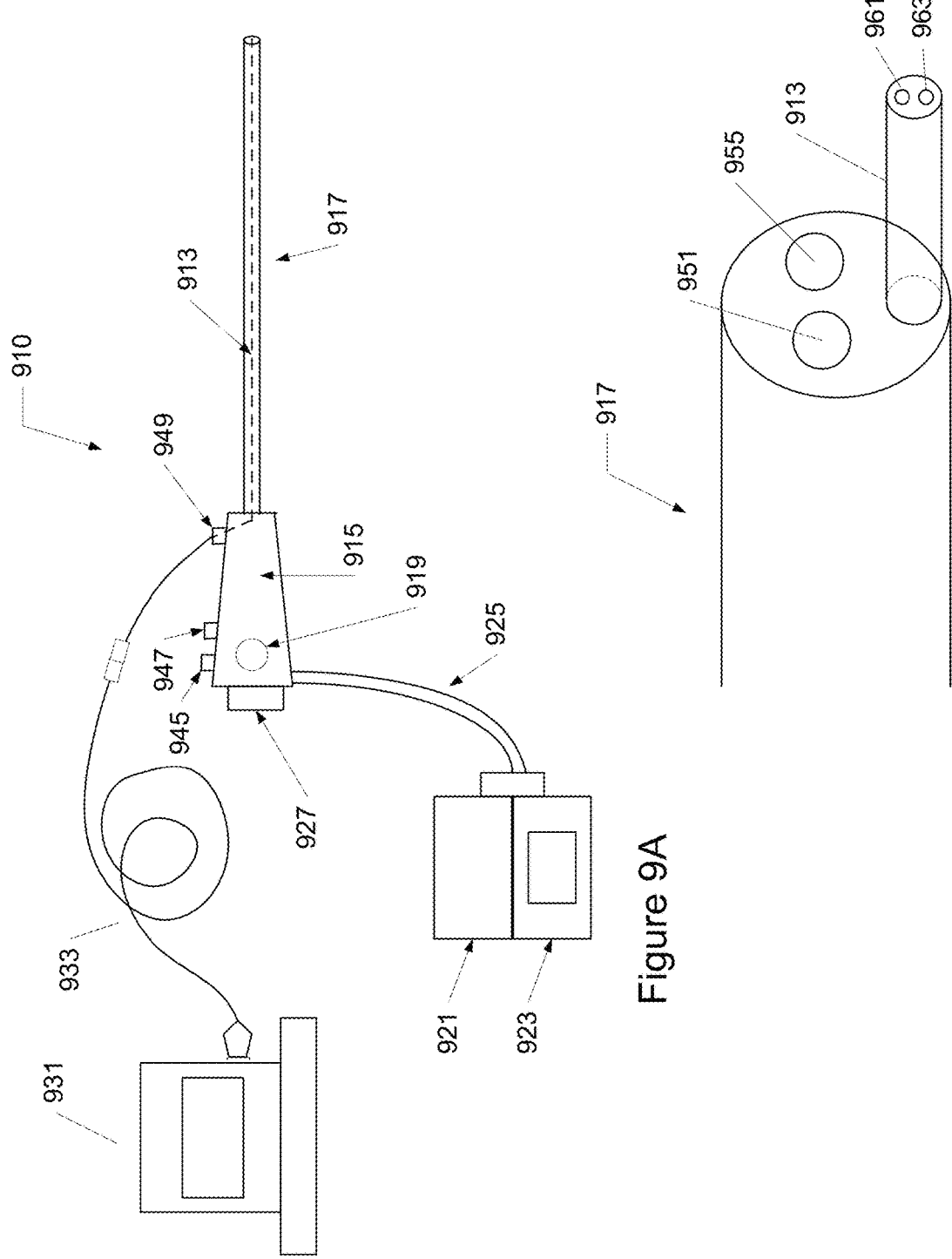

Test before resection

Colorectal resection

Anastomosis

USING AN OXIMETER PROBE TO DETECT INTESTINAL ISCHEMIA

CROSS-REFERENCE TO RELATED APPLICATIONS

This patent application is a divisional of U.S. patent application Ser. No. 15/223,788, filed Jul. 29, 2016, issued as U.S. Pat. No. 10,335,070 on Jul. 2, 2019, which is a divisional of U.S. patent application Ser. No. 12/410,155, filed Mar. 24, 2009. These applications are incorporated by reference along with all other references cited in this application.

BACKGROUND OF THE INVENTION

The invention relates to the field of medical devices, their use and manufacture, and more specifically to medical devices and techniques for diagnosing intestinal ischemia or bowel ischemia.

Intestinal ischemia or bowel ischemia is a term used to describe the result of a variety of disorders that cause insufficient blood flow to the gastrointestinal tract. Ischemia can be localized to a relatively small part of the small intestine or large intestine, or it may be widespread and involve both types of intestines. Moreover, ischemic necrosis (i.e., localized death of living cells) of the intestine can be superficial, involving mucosa (inner lining) to full thickness transmural necrosis. Intestinal ischemia can manifest with symptoms ranging from a mild, short-lived abdominal pain, to bloody diarrhea or a more serious situation that may require surgery.

There are several causes for intestinal ischemia. The most common cause is diminished intestine perfusion resulting from low cardiac output. It is often seen in patients with cardiac disease or in patients with prolonged shock of any etiology. Another cause of intestinal ischemia is an occlusive disease of the vascular supply to the intestine. The occlusive disease can result from atheroma (i.e., a deposit of lipid-containing plaques an inner wall layer of an artery), thrombosis (i.e., a stationary clot attached to the blood vessel wall), or embolism (i.e., a migrating blood clot that forms a blockage) in which the collateral circulation is not adequate to maintain intestine integrity. Another common form of intestinal ischemia is ischemic colitis, in which inflammation and injury of the colon result from inadequate blood supply.

When ischemic bowel disease severely damages tissue in the intestine, the damaged tissue must be surgically removed. The remaining tissue can be sewn together, typically in end-to-end anastomosis (i.e., surgical connection of two severed tubular organ parts). Prior to resection, a surgeon must distinguish between viable and nonviable intestinal tissue. Typically, the surgeon relies on subjective visual inspection such as tissue color to determine which intestinal tissue is viable. Such a decision is often made hastily during operation. Further, such visual inspection has been shown to be unreliable in determining long-term viability of intestinal tissue.

Determining intestine viability is difficult but important for patients with ischemic bowel disease. If nonviable tissue is not removed, the result can be fatal. Removing too much intestine can also lead to severe complications. Thus, there is a need for better medical devices and systems that can determine the oxygenation state of the entire thickness of an intestinal tissue as well as other tissues. Improved devices and system can better assist doctors in determining viability of an intestinal tissue, and the doctors can make a better informed decision regarding a treatment plan for the patient. The present invention meets this and other needs.

BRIEF SUMMARY OF THE INVENTION

In one aspect of the invention, a needle sensor device includes a hollow needle and a sensor probe disposed inside the hollow needle. A beveled edge of the hollow needle can be used to puncture a tissue, such as an outer tissue of an abdomen, to introduce the needle sensor device inside the abdomen to measure oxygen saturation of a serosal surface of the intestine or mesentery.

The sensor probe has one or more optical fibers where distal ends of the optical fibers form an oximeter sensor at its tip, which allows measuring of oxygen saturation of a tissue. In one embodiment, the one or more optical fibers include a first optical fiber and a second optical fiber, which are separated by a given distance so that the sensor probe is configured to measure oxygen saturation value from a full thickness of an intestinal wall tissue. For example, distal ends of the first and second optical fibers are separated by a distance of about 2 millimeters or less.

In another aspect of the invention, a system includes a needle sensor device and a system unit (e.g., a console) including a display, processor, signal emitter circuit, signal detector circuit, and a receptacle to couple to proximal ends of the one or more optical fibers. The signal emitter circuit sends a signal through the one or more optical fibers, and the signal detector circuit receives the signal from the one or more optical fibers. The receptacle may be removably coupled to proximal ends of the one or more optical fibers.

The signal emitter circuit may include at least one of a laser emitter or light emitting diode (LED) emitter. The signal emitter circuit may further cause an optical signal, having a wavelength from about 600 nanometers to about 900 nanometers, to be transmitted through the one or more optical fibers through sensor openings at the tip of the sensor probe. Furthermore, the signal emitter circuit may cause an optical signal having a two or more different wavelengths to be transmitted through the sensor openings.

A first wavelength of the two or more different wavelengths may be about 690 nanometers. A second wavelength of the two or more different wavelengths may be about 830 nanometers.

In an embodiment to measure oxygen saturation of tissue touching the tip of device, the system unit determines a first quantity corresponding to an intensity of light of a first wavelength transmitted from a first sensor opening of the tip through the tissue to a second sensor opening of the tip. The system unit also determines a second quantity corresponding to an intensity of light of a second wavelength transmitted from the first sensor opening of the tip through the tissue to the second sensor opening of the tip, where the second wavelength is different from the first wavelength. Then the system unit calculates an attenuation ratio of the first quantity to the second quantity.

In yet another aspect of the invention, a method includes puncturing an outer tissue with a needle sensor device. The needle sensor device contacts an intestinal or mesentery tissue with the tip of the sensor probe, transmitting a first light, having a wavelength between about 600 nanometers to about 900 nanometers, into the tissue through the tip of the sensor probe, and receiving a second light reflected from the tissue through the tip of the sensor probe. Then an oxygen saturation value for the tissue is determined based on values for the first and second light.

In yet another aspect of the invention, a method includes puncturing an outer tissue with a trocar. The needle sensor device is introduced into an abdominal cavity through the trocar. The method includes contacting an intestinal or mesentery tissue with the tip of the sensor probe, transmitting a first light, having a wavelength between about 600 nanometers to about 900 nanometers into the tissue through the tip of the sensor probe, and receiving a second light reflected from the tissue through the tip of the sensor probe. Then an oxygen saturation value for the tissue is determined based on values for the first and second light.

In yet another aspect of the invention, a method includes inducing a temporary ischemic period for an intestinal or mesentery tissue of a patient by constricting a mesenteric artery that supplies blood to the tissue. The method includes measuring oxygen saturation of the tissue during the temporary ischemic period and analyzing the oxygen saturation of the tissue during the temporary ischemic period. The patient can be diagnosed as having intestinal ischemia according to changes in the oxygen saturation in the tissue during the temporary ischemic period.

In yet another aspect of the invention, a system includes a device for inducing a temporary ischemic period in an intestinal or mesentery tissue, a sensor probe that measures oxygen saturation of the tissue during the temporary ischemic period, and a system unit coupled to the sensor probe, that analyzes oxygen saturation in the tissue during the temporary ischemic period and diagnoses the patient as having intestinal ischemia according to the oxygen saturation in the tissue during the temporary ischemic period.

In yet another aspect of the invention, a method includes inducing a temporary ischemic period for an intestinal or mesentery tissue of a patient by constricting a mesenteric artery that supplies blood to the tissue, measuring oxygen saturation of the tissue during a recovery from the temporary ischemic period, after removing a constriction to the mesenteric artery, analyzing the oxygen saturation of the tissue during recovery, and diagnosing the patient as having intestinal ischemia according to changes in the oxygen saturation in the tissue during the recovery.

In yet another aspect of the invention, a system includes a device for inducing a temporary ischemic period in an intestinal or mesentery tissue, a sensor probe that measures oxygen saturation of the tissue during recovery from the temporary ischemic period, and a system unit, coupled to the sensor probe, that analyzes oxygen saturation in the tissue during the recovery and diagnoses the patient as having intestinal ischemia according to the oxygen saturation in the tissue during the recovery.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 3A shows a system of the invention including a monitoring console, a catheter device, and a cable connecting the catheter device to the monitoring console.

FIG. 3B shows a distal end surface of the catheter device shown in FIG. 3A, where distal ends of two optical fibers form an oximeter sensor.

FIG. 9A shows an endoscopic device with a sensor probe inserted into an instrument channel of the endoscopic device.

FIG. 9B shows a tip of an elongated shaft of the endoscopic device where a sensor probe can be extended beyond a distal end surface of the elongated shaft.

DETAILED DESCRIPTION OF THE INVENTION

Figure 1:
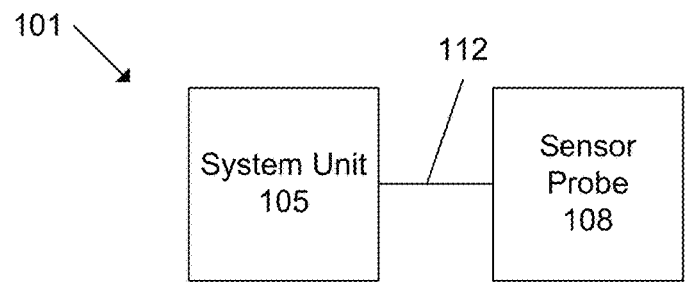
FIG. 1 shows a block diagram of an oximeter system for measuring oxygen saturation of tissue in a patient.

When blood supply to a tissue or organ within a body is diminished due to a poor circulation or blockage of blood vessels, the tissue or organ suffers ischemia which results in diminished functioning of the tissue or organ. The tissue or organ ischemia can present various symptoms in a patient which makes a proper diagnosis of the underlying disease difficult for a doctor. Consequently, an ischemic disease is often not diagnosed until an advanced stage, which limits treatment options for the patient.

This is particularly the case for a patient suffering with intestinal ischemia. The ischemic condition or oxygenation state of an internal organ, such as the intestine or mesentery, is difficult to evaluate. The intestine is a long tubular organ which can stretch about 7 feet long. The mesentery is a fold of tissue which anchors the intestine to the back of the abdominal wall. Blood vessels, nerves, and lymphatics branch through the mesentery to supply the intestine. Since the intestine and mesentery involve an extensive network of tissues, it is difficult to localize an ischemic area in the tissue.

The present invention provides various medical devices and systems for measuring oxygen saturation of a tissue located inside a body. In particular, the devices and systems can be used to measure oxygen saturation of mouth, esophagus, stomach, small intestine, large intestine, mesentery, anus, or others. While some of these body parts may be classified as organs, for this application, "tissue" and "organ" are used interchangeably to refer to any body part or aggregate of cells. In other words, "tissue" may be used to refer to an organ, and vice versa.

The medical devices and systems in accordance with embodiments of the invention include a catheter device, an endoscopic device, and a needle sensor device which allow the doctor to explore tissues deep inside a body noninvasively or with a minimal pin size puncture. In embodiments of the invention, the devices include a sensor probe that has one or more optical fibers that form an oximeter at a distal end of the sensor probe. As the devices are guided down along the gastrointestinal tract, the oximeter sensor of the sensor probe can contact a tissue and measure oxygen saturation at various locations along the tract.

In embodiments of the invention, the sensor probe is connected to a signal emitter which sends light having a wavelength between about 600 nanometers to about 900 nanometers through optical fibers in the sensor probe into a tissue. After being scattering and absorbed by chromophores (e.g., hemoglobin) in the tissue, an attenuated version of the light is detected by the sensor probe and is transmitted to a photodetector. Based on values of the initial light and the attenuated version of the light, an oxygen saturation value of the tissue can be obtained. Based on the oxygen saturation value of the tissue, it can be determined whether the tissue is suffering from ischemia.

Embodiments of the invention can be used in a wide variety of applications. One application is in diagnosing whether or not a patient has intestinal ischemia. Moreover, the devices and systems can be used to determine the severity of intestinal ischemia and the extent of tissue damage. In another application, the devices and systems can be used in monitoring oxygen saturation of an intestinal tissue or mesentery during a surgical procedure (e.g., anastomosis). Since oxygen saturation measurements can be made in real-time during surgery, any necessary modifications to surgical procedures can be made based on oxygen saturation measurements. Furthermore, the devices and systems can also be used during recovery after surgery to evaluate a patient's prognosis.

Embodiments of the present invention provide several advantages. The catheter and endoscopic devices can be inserted into a human body noninvasively to determine the oxygenation state of a mucosal surface of the intestine or any other tissue along the gastrointestinal tract. Moreover, the sensor needle device can be introduced into an abdomen with a pin size hole to determine the oxygenation state of a serosal surface of the intestine or mesentery. These devices cause minimal discomfort to the patient and rarely cause any medical complications.

Moreover, the devices and systems according to embodiments of the invention provide oxygen saturation measurements of the entire thickness of the intestine, not just an outer skin or superficial surface of the intestine. An oximeter sensor of the present devices and systems also directly contact a tissue to make oxygen saturation measurements of the tissue. Thus, the oxygen saturation measurements according to embodiments of the invention can assess the oxygenation state of the intestine more accurately.

Further, sensor probes, catheter devices, and sensor needle devices of the present invention are cost effective to manufacture since they include mostly optical fibers and do not contain parts such as light emitting diodes or photodiodes, which are relatively expensive. The cost effectiveness is important as the devices containing a sensor probe are typically disposed after a single use. Also, since the portion of a device that is introduced into a body cavity does not include electrical components such as light emitting diodes, photodiodes, or electrical wires, there is no risk that internal organs will get an electrical shock, heated, or burned by the device.

Examples of embodiments of the invention are illustrated using figures and are described below. The figures described herein are used to illustrate embodiments of the invention, and are not in any way intended to be restrictive of the broad invention. Embodiments of the invention are not limited to the specific arrangements and constructions shown and described. For example, features shown in one figure can be combined with features shown in another figure.

FIG. 1 shows an oximeter system 101 for measuring oxygen saturation of a tissue in a patient. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers), or any combination of these or other types of connections. In other implementations of the invention, however, connection 112 may be wireless such as via a radio frequency (RF) or infrared communication.

Typically, the system is used by placing the sensor probe in contact or close proximity to tissue (e.g., intestine or mesentery) at a site where oxygen saturation or other related measurement is desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heart beat. A tissue oximeter of the invention is applicable to many areas of medicine and surgery including plastic surgery and spinal surgery. The tissue oximeter can make oxygen saturation measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, 7,247,142, and 7,355,688. These patents are assigned to the same assignee as this patent application and are incorporated by reference along with all other references cited in this application.

Various equations for self-calibration schemes are also known in the art. Self-calibration schemes are used to adjust for system factors such as source intensity, detector gain, and loss of light in the optical fibers and connectors. The self-calibration scheme may include equations discussed in U.S. Pat. Nos. 6,516,209, 6,735,458, and 6,078,833, and *New Optical Probe Designs for Absolute (Self-Calibrating) NIR Tissue Hemoglobin Measurements*, Proc. SPIE 3597, pages 618-631 (1999), which are incorporated by reference.

The attenuation ratio method may also include techniques discussed in U.S. Pat. No. 6,587,701, which is incorporated by reference. The attenuation ratio method is used to determine tissue oxygenation, hemoglobin concentration, or both. Additional detail on self-calibration schemes and attenuation ratio methods is also discussed in U.S. patent application Ser. No. 12/126,860, filed May 24, 2008, which is incorporated by reference.

Figure 2:
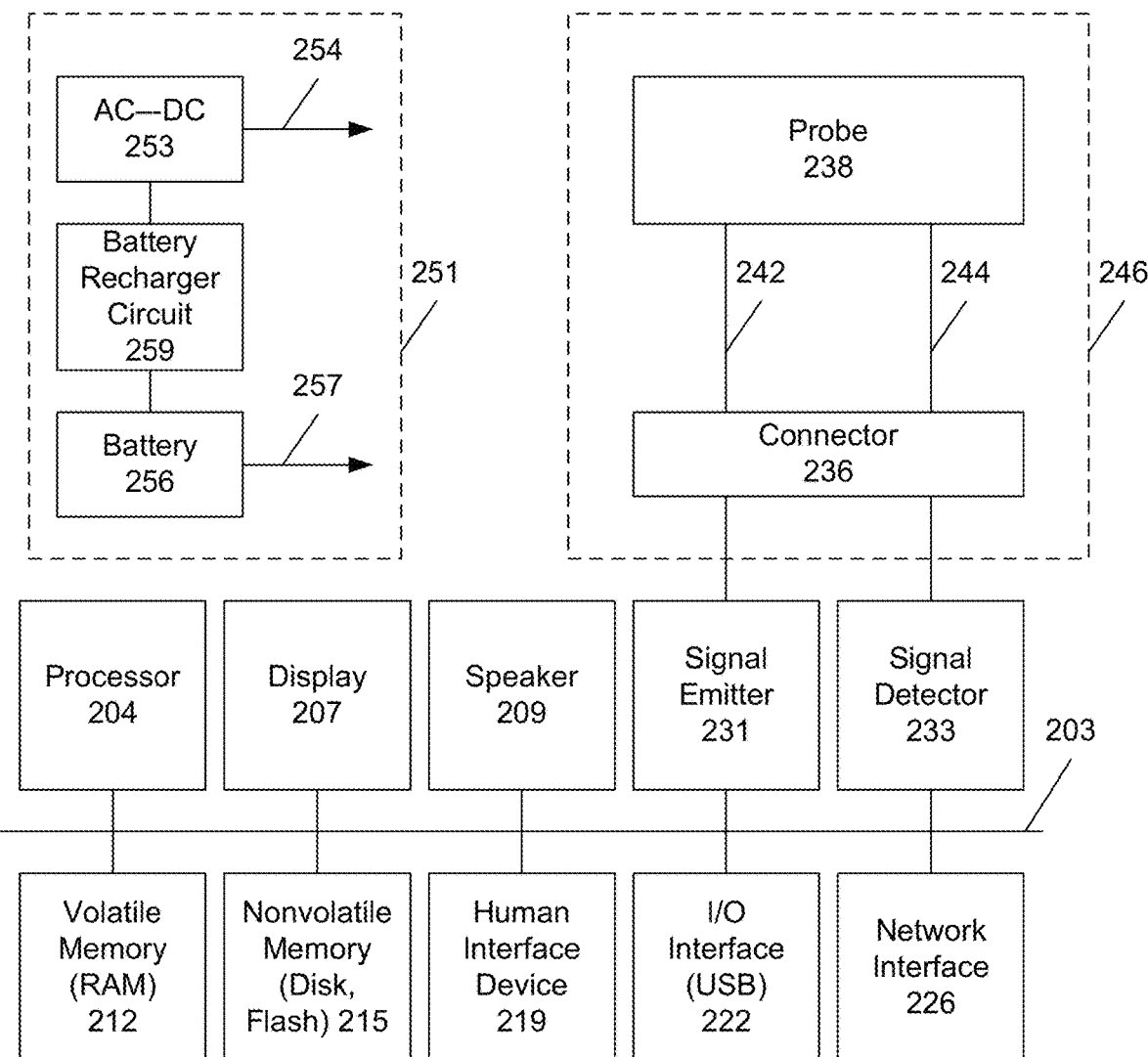
FIG. 2 shows a more detailed block diagram of a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires.

Signal emitter 231 is a light source that emits light at one or more specific wavelengths. In a specific implementation, two wavelengths of light (e.g., 690 nanometers and 830 nanometers) are used. In other implementations, other wavelengths of light may be used. The signal emitter is typically implemented using a laser diode or light emitting diode (LED). Signal detector 233 is typically a photodetector capable of detecting the light at the wavelengths produced by the signal emitter.

The connector may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. When a probe is inserted, the system uses the second keying feature to determine which type of probe is connected to the system. Then the system can perform the appropriate functions, use the proper algorithms, or otherwise make adjustments in its operation for the specific probe type.

For example, when the system detects a cerebral probe is connected, the system uses cerebral probe algorithms and operation. When the system detects a thenar probe is connected, the system uses thenar probe algorithms and operation. A system can handle any number of different types of probes. There may be different probes for measuring different parts of the body, or different sizes or versions of a probe for measuring a part of the body (e.g., three different thenar probe models).

With the second keying feature, the system will be able to distinguish between the different probes. The second keying feature can use any type of coding system to represent each probe including binary coding. For example, for a probe, there are four second keying inputs, each of which can be a logic 0 or 1. With four second keying inputs, the system will be able to distinguish between sixteen different probes.

Probe 246 may be a handheld tool and a user moves the probe from one point to another to make measurements.

However, in some applications, probe 246 is part of an endoscopic instrument or robotic instrument, or both. For example, the probe is moved or operated using a guiding interface, which may or may not include haptic technology.

In various implementations, the system is powered using a wall outlet or battery powered, or both. Block 251 shows a power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected to the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version (e.g., computer program product) of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

FIG. 3A shows a schematic diagram of a specific implementation of a system. Shown in FIG. 3A is a system 300 that includes a catheter device 303 which contains a sensor probe 333 with an oximeter sensor at its distal end. The catheter device has a shaft portion 305 and a connector 311. The catheter device is connected to a console 306 via a cable 309. Connector 311 at a proximal end of the catheter device is connected to a connector 313 of cable 309. The cable is connected to a receptacle 315 which is located at the console.

Shaft portion 305 of the catheter device is typically flexible, and can be of any suitable length. For example, the shaft of the catheter device can have a length of about 5 centimeters to about 10 meters, or any length between these lengths. The selection of a shaft length depends on the end use of the catheter device. For example, when the catheter device is used to examine an esophagus area of a patient, a relatively short catheter device (e.g., 20 centimeters in length) can be used. When examining a small intestine area of a patient, a relatively long catheter device (e.g., 7 meters in length) is used since the catheter device travels a long distance to the small intestine from the insertion point (e.g., mouth or anus).

In one implementation of the invention, the catheter device may have markings on an outer surface of the shaft. For example, the outer surface of the shaft may have markings at intervals of every 10 millimeters starting at a distal end of the shaft (e.g., 10, 20, 30 millimeters, and so forth). The markings on the outer surface of the shaft can assist a doctor to determine a length of the shaft that is inserted into a body cavity and where the distal end of the catheter device is located during an exploratory procedure.

A diameter of the catheter device can be of any suitable dimension depending on its end application. For example, the diameter of the catheter device can vary between about 1 to 20 millimeters, more typically between about 1.5 to 10 millimeters, even more typically between about 2 to 5 millimeters. When the catheter device is inserted into the mouth of a patient, it is desirable to minimize the diameter of the catheter device for the patient's comfort. However, it may be desirable to use a catheter device with a larger diameter, since a larger catheter device can hold optical fibers having a larger diameter, which may result in stronger optical signals.

FIG. 3B illustrates a perspective view of a distal end of one embodiment of a catheter device 330. The catheter device contains sensor probe 333 having a first optical fiber 323 and a second optical fiber 325 along a longitudinal axis of the shaft of the catheter device. Sensor probe 333 is surrounded by an outer sheath 321 which provides a structural integrity and protection for the sensor probe. Typically, distal ends of the optical fibers are exposed at the tip of the catheter device. The proximal ends of the optical fibers (not shown in FIG. 3B) are connected to a console through a cable.

As shown in FIG. 3B, distal ends of optical fibers 323 and 325 are held in place by a filler material 327. The filler material separates and fixes distal ends of the optical fibers by a suitable distance to optimize optical signaling for a given tissue. The filler material may extend the entire length of the shaft; alternatively, the filler material may be applied only at the distal end of the catheter device to firmly fix the distal ends of the optical fibers.

Any suitable filler material can be used as long as it is chemically and structurally stable, and does not interfere with transmission of optical signals in the optical fibers. For example, the filler material can be epoxy. The epoxy material can be cured around the distal ends of the optical fibers. Alternatively, the entire length of the shaft of the catheter device can be filled with an epoxy or other material, and then a suitable number of channels can be burrowed in the filler material to thread the optical fibers through.

Outer sheaths of catheter devices are formed of a flexible, durable material such as a medical grade polytetrafluoroethylene (PTFE). The PTFE tubing can be easily advanced around curves of body cavities and is substantially impervious to body fluids. Sensor probes in embodiments of the invention can be incorporated in commercially available catheter outer sheaths having any suitable diameters.

In one implementation, first optical fiber 323 is connected to a signal emitter circuit via a cable interface, and second optical fiber 325 is connected to a signal detector circuit via a cable interface. Light generated by the signal emitter (e.g., a radiation source such as laser diode, photodiodes) travels down the first optical fiber and is transmitted into a tissue. After the light enters the tissue, light scatters due to the heterogeneous structure of the tissue, and some of the light is absorbed by chromophores such as hemoglobin. An attenuated version of the light that is reflected from the tissue is detected by the second optical fiber and is transmitted to the signal detector (e.g., a photodetector).

Generally, the tip of a sensor probe contacts a tissue to measure optical characteristics of a tissue, such as tissue oxygen saturation. For example, oxygen saturation of the tissue can be calculated based on a value of the initial light generated by the signal emitter and a value of an attenuated version of the light that is reflected from the tissue.

The tip of a sensor probe with distal ends of the optical fibers is referred to as "an oximeter sensor." A cross section area of an optical fiber at the distal end of the sensor probe is referred to as "a source structure" when it is configured to transmit light into a tissue. A cross section area of an optical fiber at the distal end of the sensor probe is referred to as "a detector structure" when it is configured to receive reflected light from the tissue. The source structure and detector structure may be collectively referred to as "openings" or "sensor openings" as they allow passage of light traveling from optical fibers to a tissue (and reflected light from the tissue back to the optical fibers). Further, a distance between the openings (e.g., between a source structure and a detector structure) is typically calculated from a center of one opening to a center of another opening.

The optical fibers in the sensor probe can have any suitable diameters. For example, a diameter of an optical fiber can be between about 0.1 millimeters to about 2 millimeters, typically between about 0.5 millimeters to about 1.5 millimeters, even more typically between about 0.5 millimeters to about 1 millimeter, or any other diameter between these dimensions. The selection of the optical fiber diameter may depend on many factors. For example, if it is desired to build a catheter device with a narrow shaft, then it is desirable to use optical fibers with a smaller diameter. Typically, loss of signal transmission is greater with optical fibers with a smaller diameter. Thus, a desire to produce a catheter device with a smaller diameter needs to be balanced against optimizing signal transmission through the optical fibers.

The depth of light penetration into a tissue depends on, among other factors, a distance between a source structure and detector structure at the distal end of the sensor probe. As shown in FIG. 3B, optical fiber 323 and optical fiber 325 are separated by a distance of X. The depth of light penetration increases with an increasing distance of X. Thus, for measuring oxygen saturation of a thin layer of tissue or a shallow volume of tissue, it may be desirable to use a sensor probe with a smaller separation between a source structure and a detector structure (e.g., X being equal to 1 millimeter or less). For measuring oxygen saturation of a thick layer of tissue, it may be desirable to use a sensor probe with a larger separation between a source structure and a detector structure.

For measuring oxygen saturation of a thin layer of tissue, such as an intestine, the distance between a source structure and a detector structure at the tip of a sensor probe is relatively small. It is desirable that the distance between the two structures is adjusted so that light penetrates the entire wall thickness of the intestine, but not other surrounding tissues. Typically, the intestinal wall is about 2 millimeters thick. Thus, it is desirable that the distance between a source structure and a detector structure at the tip of a sensor probe is optimized to penetrate the entire thickness of the intestinal wall. For example, the distance between the two structures in the sensor probe can be between about 0.2 millimeters to about 3 millimeters, more typically between about 0.5 millimeters to about 2 millimeters, even more typically between about 0.5 millimeters to about 1 millimeter, or any number between these dimensions.

Console 306 (sometimes referred to as a system unit) typically includes a display, processor, signal emitter circuit, signal detector circuit, and a receptacle to couple to proximal ends of the one or more optical fibers. The signal emitter sends a signal through an optical fiber and the signal detector circuit receives the signal from the same or different optical fiber. The receptacle may be removably coupled to proximal ends of the first and second optical fibers.

A display screen on the console can display the patient's data, such as oxygen saturation measurements and the locations in the intestine or mesentery from which the measurements were made.

The console may also include a mass storage device to store data (e.g., hard disks, CD-ROM drive, DVD-ROM drive, flash storage drive, or others). The stored data may include patient information, other identifying information, patient medical history, oxygen saturation measurements and the time and data measured.

In one implementation, a discrete wavelength of light (as opposed to a broad band of light that includes many wavelengths of light, such as white light) is generated by a radiation source. One or more discrete wavelengths of light can be generated by one or more radiation sources.

In a specific implementation, the console includes a first radiation source and a second radiation source. The radiation sources may be dual wavelength light sources. In other words, first radiation source provides two wavelengths of radiation and second radiation source provides two wavelengths of radiation. First radiation source, second radiation source, or both may include one or more laser diodes or light emitting diodes (LEDs) that produce light in any wavelength, but typically the wavelengths range from about 600 nanometers to about 900 nanometers. In a specific implementation, a first wavelength of light is generated that has a wavelength of about 690 nanometers. A second wavelength of light is generated that has a wavelength of about 830 nanometers.

In a specific implementation, the signal emitter circuit may include one or more laser emitters, light emitting diode (LED) emitters, or both. The signal emitter circuit may be used to generate an optical signal having two or more different wavelengths to be transmitted through the sensor unit. The wavelengths may range from about 600 nanometers to about 900 nanometers.

In a specific implementation, one or more near-infrared radiation sources are included within the console. In other implementations, the radiation sources may be external to the console. For example, the radiation sources may be contained within a separate unit between the console and sensor probe. In yet another implementation, some radiation sources may be within the console while other radiation sources are external to the console.

These radiation sources may be near-infrared lasers. In a specific implementation, there is one near-infrared laser located within the console. In other implementations, there may be more than one near-infrared laser. For example, there may be 2, 3, 4, 5, 6, 7, 8, 9, or 10, or more than 10 radiation sources. In another implementation, the radiation sources may also include those that produce light in a visible spectrum. In one implementation, a beam combiner can be used to merge light from different radiation sources. The merged light can then be provided via output fibers.

In a specific implementation, a single pulse of light is transmitted into the tissue. In another implementation, multiple pulses of light may be transmitted into the tissue. For example, a first pulse of light may be received by a first detector. A second pulse of light may be received by a second detector.

While FIG. 3B illustrates an embodiment with two optical fibers in the sensor probe, any suitable number of optical fibers can be contained in the sensor probe. For example, there may be one, two, three, four, five, six, seven, or eight or more optical fibers. Any one or more optical fibers in the sensor probe can be connected to a light source to transmit light; any one or more optical fibers in the sensor probe can be used to receive light reflected from the tissue.

Figure 4A:
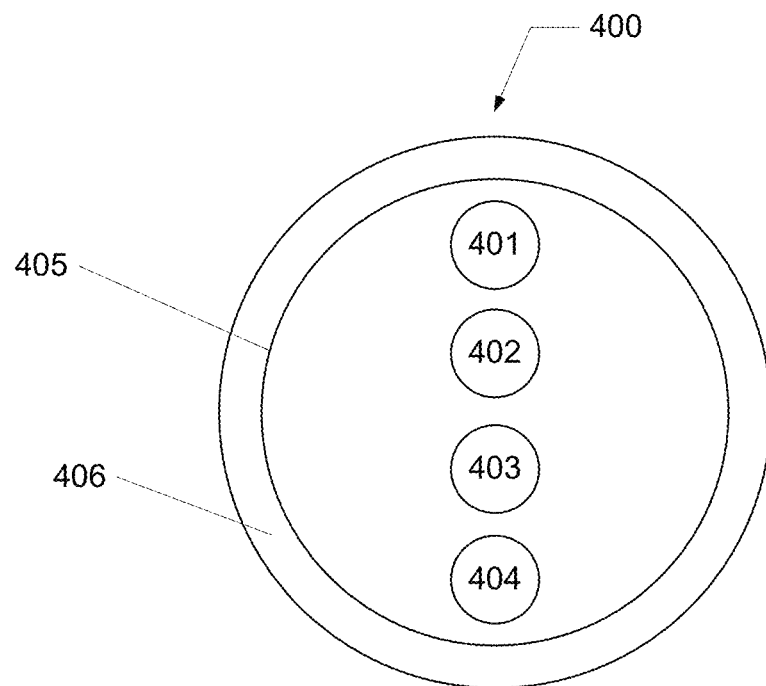
FIG. 4A shows a distal end surface of a catheter device having four sensor openings in a linear array.
Figure 4B:
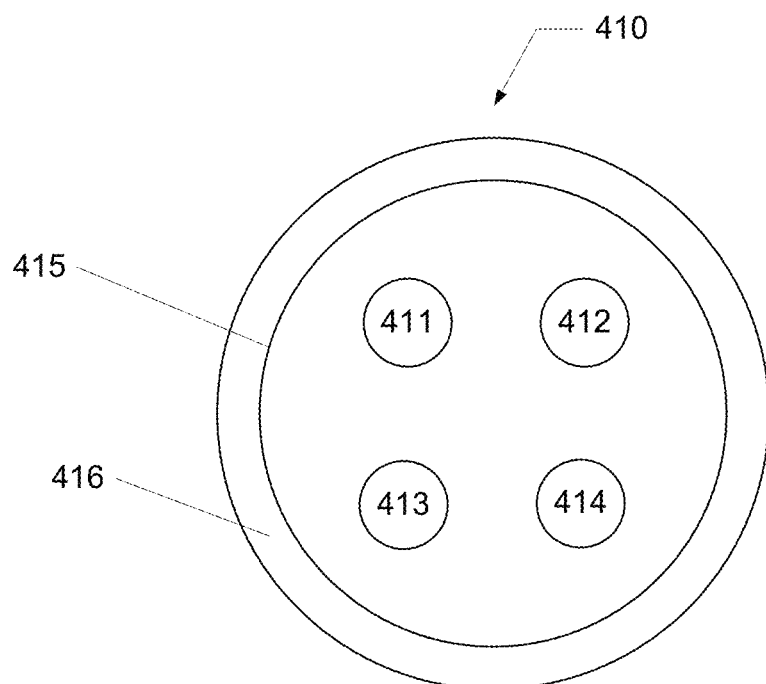
FIG. 4B shows a distal end surface of a catheter device having four sensor openings forming a square.
Figure 4C:
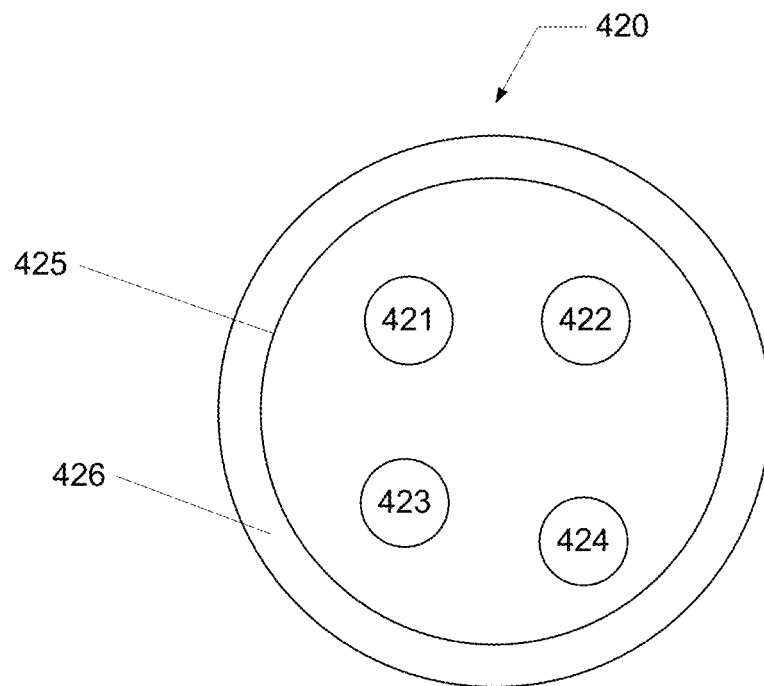
FIG. 4C shows a distal end surface of a catheter device having four sensor openings forming a quadrilateral, where a line drawn between a first sensor opening and a second sensor opening is not parallel to a line drawn between a third sensor opening and a fourth sensor opening.

FIGS. 4A through 4C illustrate examples of different arrangements of source structures and detector structures at a distal end of a catheter device.

FIG. 4A shows a distal end of a catheter device 400 where a sensor probe 405 includes four openings 401-404. The sensor probe is surrounded by an outer sheath 406. As shown, the four openings are arranged in a linear array. In one implementation, openings 401 and 402 are sensor structures and openings 403 and 404 are detector structures. In another implementation, the distance between openings 401 and 402 is equal to the distance between openings 402 and 403; this distance is also equal to that between openings 403 and 404. While the four sensor openings shown in FIG. 4A are equal in size, one or more sensor openings can have different diameters.

While FIG. 4A shows that four sensor openings are in a linear array, in another implementation, any three of the openings may be positioned in a linear array at the tip of the sensor probe. For example, the oximeter sensor may include a first sensor emitter opening (i.e., a source structure), a second sensor emitter opening, a first sensor detector opening (i.e., a detector structure), and a second sensor detector opening. Any three of the openings may be positioned in a linear arrangement at a distal end of the sensor probe.

In a specific embodiment, the second sensor emitter opening is between the first sensor emitter opening and the first sensor detector opening, and the first sensor detector opening is between the second sensor emitter opening and the second sensor detector opening.

The first sensor detector opening may be spaced away from the second sensor detector by about 5/3 millimeters or less, and the first sensor detector opening may be spaced away from the second sensor emitter opening by about 5/3 millimeters or less.

FIG. 4B illustrates a distal end of another catheter device 410 where a sensor probe 415 includes four sensor openings 411-414. The sensor probe is surrounded by an outer sheath 416. In an implementation, the distances between openings 411-412, 412-414, 413-414, and 413-411 are all equal. Thus, in this implementation, openings 411, 412, 413, and 414 form the vertices of a square. In other implementations, however, four openings may form the vertices of any quadrilateral, such as a rectangle, a rhombus, a trapezoid, or a parallelogram.

FIG. 4C illustrates a distal end of yet another catheter device 420 which is a variation of the implementation of the sensor probe shown in FIG. 4B. Shown in FIG. 4C is a catheter device 420 where a sensor probe 425 includes four sensor openings 421-424. The sensor probe is surrounded by an outer sheath 426. The four openings are positioned asymmetrically such that a line drawn through openings 421 and 422 is not parallel to a line through openings 423 and 424.

Additionally, the distance between openings 421 and 422 is shorter than the distance between openings 423 and 424. Thus, in FIG. 4C, the distance between openings 421 and 423 does not equal to the distance between openings 422 and 424 and the distance between openings 422 and 423 does not equal to that between openings 422 and 424.

In the implementations discussed so far, each sensor opening of the sensor probe has a single optical fiber associated with it. However, in other implementations of the invention, each sensor opening of the sensor probe may have multiple fibers—two or more—associated with it. Alternatively, each opening of the probe may have multiple light paths or light channels associated with it.

Figure 5:
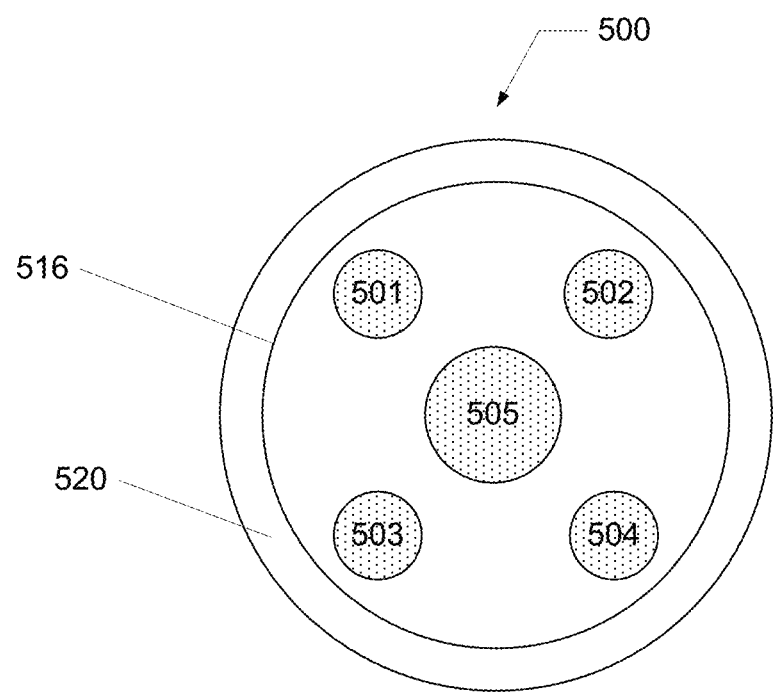
FIG. 5 shows a distal end surface of a catheter device having five sensor openings, where each sensor opening includes a fiber optic bundle.

FIG. 5 shows a catheter device 500 with a sensor probe 516 that has a fiber optic bundle in each sensor opening. Each fiber optic bundle consists of two or more optical fibers mechanically bonded together, instead of a single optical fiber. Sensor probe 516 has five sensor openings 501-505 where each sensor opening has a fiber optic bundle.

In an implementation, the fiber optic bundles in openings 501-504 can be used to transmit light into a tissue, and the fiber optic bundle in opening 505 can be used to receive light reflected from the tissue back to a photodetector. In another implementation, fiber optic bundle openings 501 and 502 can be used to transmit light into a tissue, and the fiber optic bundles in openings 503-505 can be used to receive light reflected back by the tissue. A number of different arrangements of sensor openings can be used to transmit light to and receive light from a tissue.

Figure 6A:
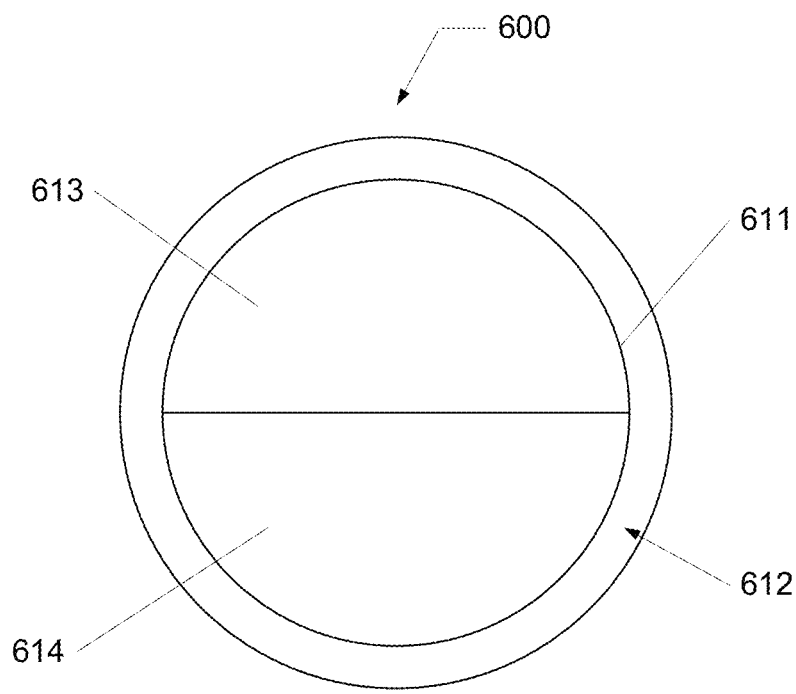
FIG. 6A shows a distal end surface of a catheter device with a single sensor opening having an optical fiber with multiple light channels.

FIG. 6A shows an implementation of a catheter device 600 where a sensor probe 612 has a single optical fiber with multiple light paths. This optical fiber may be referred to as a split channel fiber. There is a single circular fiber 611 with two semicircular light channels 613 and 614.

In a specific implementation, light channel 613 is a source channel and light channel 614 is a detector channel. For example, light channel 613 may be used to transmit light into the tissue and light channel 614 may be used to receive light from the tissue. In another implementation, light channel 613 is instead the detector channel and light channel 614 is the source channel.

Figure 6B:
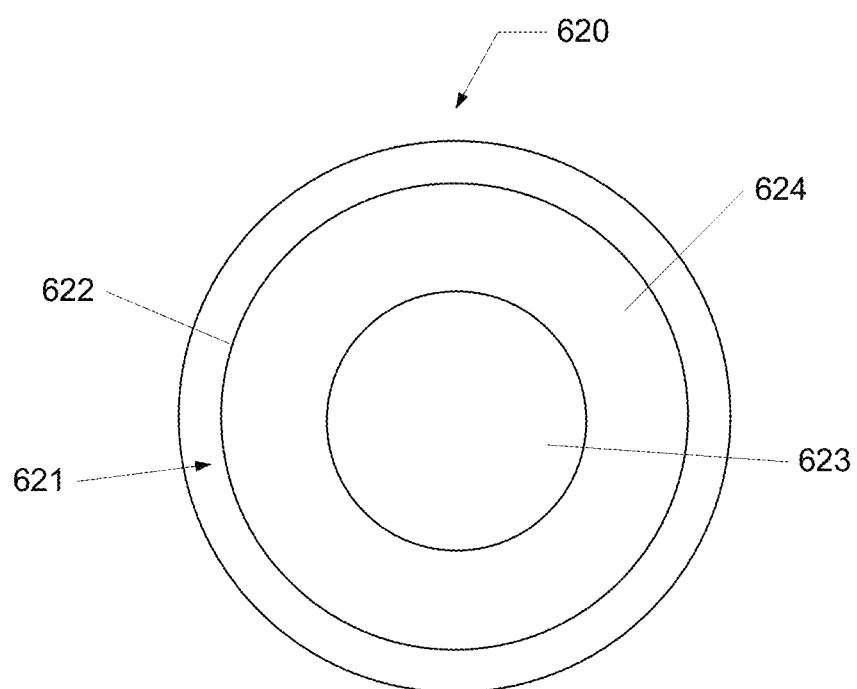
FIG. 6B shows a distal end surface of another catheter device with a single sensor opening with an optical fiber with multiple light channels.

FIG. 6B shows another implementation of a catheter device 620 with a single sensor opening 622 having an optical fiber with multiple light channels. There is a concentric core fiber 621 having an inner light channel 623, which is surrounded by an outer core light channel 624.

In a specific implementation, the inner core light channel is a source channel and the outer core light channel is a detector channel. However, in another implementation, the inner core light channel is a detector channel and the outer core light channel is a source channel.

Although light channels shown in FIGS. 6A and 6B are semicircle and concentric circles, respectively, these light channels can have any shape. Some examples of the various shapes that they may have include polygons (e.g., square, rectangle, triangle, and parallelogram), shapes with curved line segments (e.g., oval, ellipse, and crescent), or combinations of these.

Figure 7A:
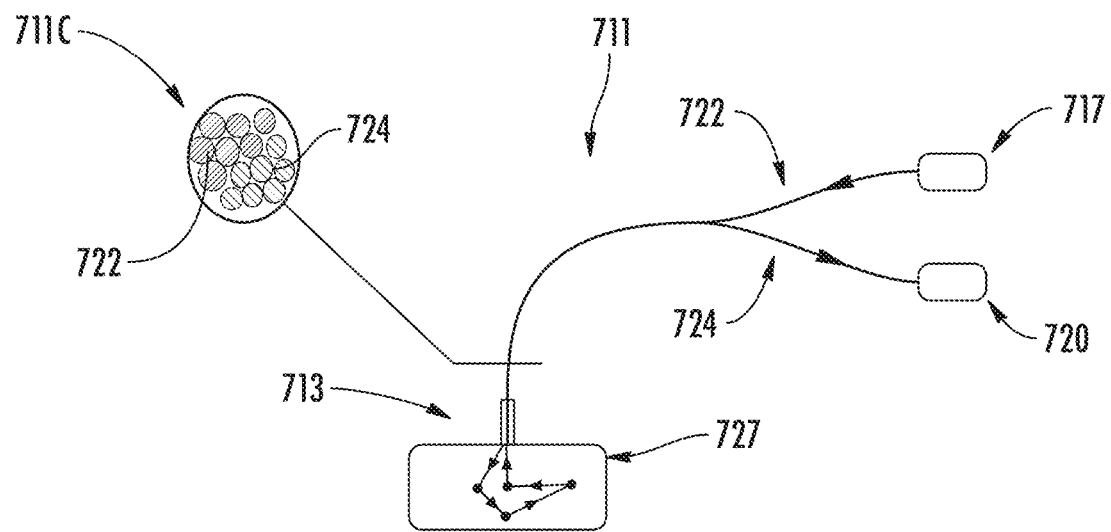
FIG. 7A shows a catheter device that has a single sensor opening at the tip and a single optical fiber bundle connected to the sensor opening at a distal end.

FIG. 7A illustrates an implementation where a single optical fiber bundle is connected to a single opening at the tip of a sensor probe. Shown in FIG. 7A is a single optical fiber bundle 711 which is connected to a single opening at the tip of a sensor probe (referred to as "probe head" 713 in FIG. 7A). A cross section of a fiber bundle 711c shows that about a half of the optical fibers in the bundle (referred to as optical fibers 722) is used for emitting light. The other half of the optical fibers in the bundle (referred to as optical fibers 724) is used for returning light.

As shown in FIG. 7A, optical fibers 722 are connected to a laser diode 717, and optical fibers 724 are connected to a photodiode 720. When light is emitted from laser diode 717, optical fibers 722 carry the light into a tissue 727. The light scatters in the tissue and is reflected back to optical fibers 724 which return an attenuated version of the light to the photodiode. The emitting light and returning light travels in the same single fiber bundle, but in opposite direction.

As shown in FIG. 7A, optical fibers 722 are connected to a laser diode 717, and optical fibers 724 are connected to a photodiode 720. When light is emitted from laser diode 717, optical fibers 722 carry the light into the tissue. The light scatters in the tissue and is reflected back to optical fibers 724 which return an attenuated version of the light to the photodiode. The emitting light and returning light travels in the same single fiber bundle, but in opposite direction.

Figure 7B:
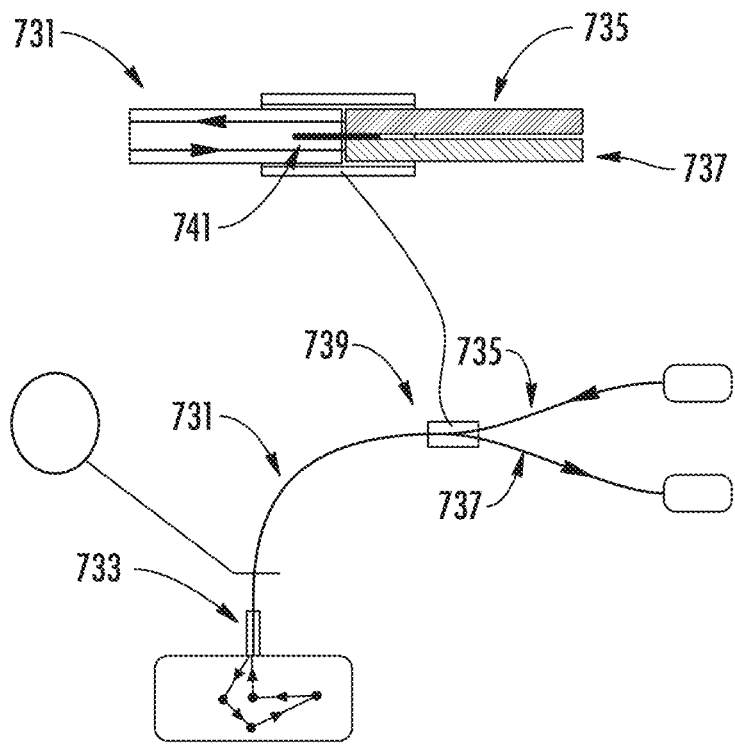
FIG. 7B shows a catheter device that has a single sensor opening at the tip and a distal end of a single optical fiber connected to the sensor opening, and a proximal end of the single optical fiber combined with two optical fibers by a fiber combiner.

FIG. 7B illustrates another implementation of the invention where a distal end of a single plastic optical fiber 731 (not a bundle) is connected to an opening at the tip of a sensor probe (referred to as "probe head" 733 in FIG. 7B). At a proximal end of single optical fiber 731, the fiber is connected to two separate optical fibers 735 and 737 by a 1-to-2 (i.e., Y-shaped) fiber or beam combiner 739. Typically, the fiber combiner contains a black separating bar 741 to reduce cross talk between the emitting light and returning light at the two surfaces between the three fibers.

FIG. 7B illustrates another implementation of the invention where a distal end of a single plastic optical fiber 731 (not a bundle) is connected to an opening at the tip of a sensor probe (referred to as "probe head" 733). At a proximal end of single optical fiber 731, the fiber is connected to two separate optical fibers 735 and 737 by a 1-to-2 (i.e., Y-shaped) fiber or beam combiner 739. Typically, the fiber combiner contains a black separating bar 741 to reduce cross talk between the emitting light and returning light at the two surfaces between the three fibers.

In the implementations shown in FIGS. 7A and 7B, the returning light is mainly light back scattered by hemoglobin in the outer, superficial surface of a tissue and a shallow volume of the tissue underneath the outer surface. This is because a distance between an emitting optical fiber and returning optical fiber is less than the diameter of the optical fiber bundle (e.g., 1 millimeter). The light being returned has not traveled deeply into the tissue. Therefore, the returning light carries more information about oxygen saturation level of the outer surface of a tissue and a shallow volume of the tissue underneath, not a whole block of tissue deep underneath the outer surface. Accordingly, the implementations shown in FIGS. 7A and 7B are particularly useful in measuring oxygen saturation of a thin layer of tissue.

In the implementations discussed so far, distal ends of optical fibers in the catheter devices are located at a flat end surface of the catheter device. However, distal ends of the optical fibers may be located at any other suitable locations in the catheter device. For example, distal ends of the optical fibers may be located at a peripheral surface (i.e., around the circumference) of the catheter device at its tip.

Figure 8A:
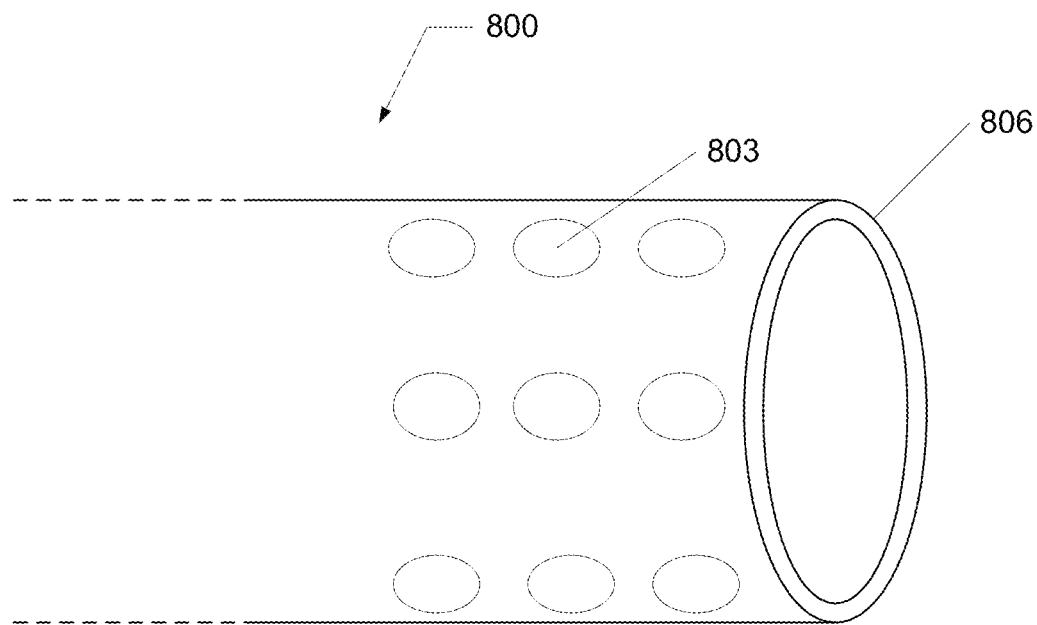
FIG. 8A shows a catheter device with distal ends of optical fibers located at a peripheral surface at the tip of the catheter device.

FIG. 8A illustrates a catheter device 800 that includes multiple optical fibers, where distal ends 803 (i.e., sensor openings) of the optical fibers are located at a peripheral surface of the catheter device at its tip, rather than at a flat end surface of the catheter device. The outer sheath of the catheter device has a number of openings, at which distal ends of the optical fibers are attached. The distal ends of the optical fibers are affixed to the openings in the outer sheath using epoxy or other suitable filler material. While nine sensor openings are shown in FIG. 8A, any suitable number of sensor openings may be present at the tip of the catheter device.

Figure 8B:
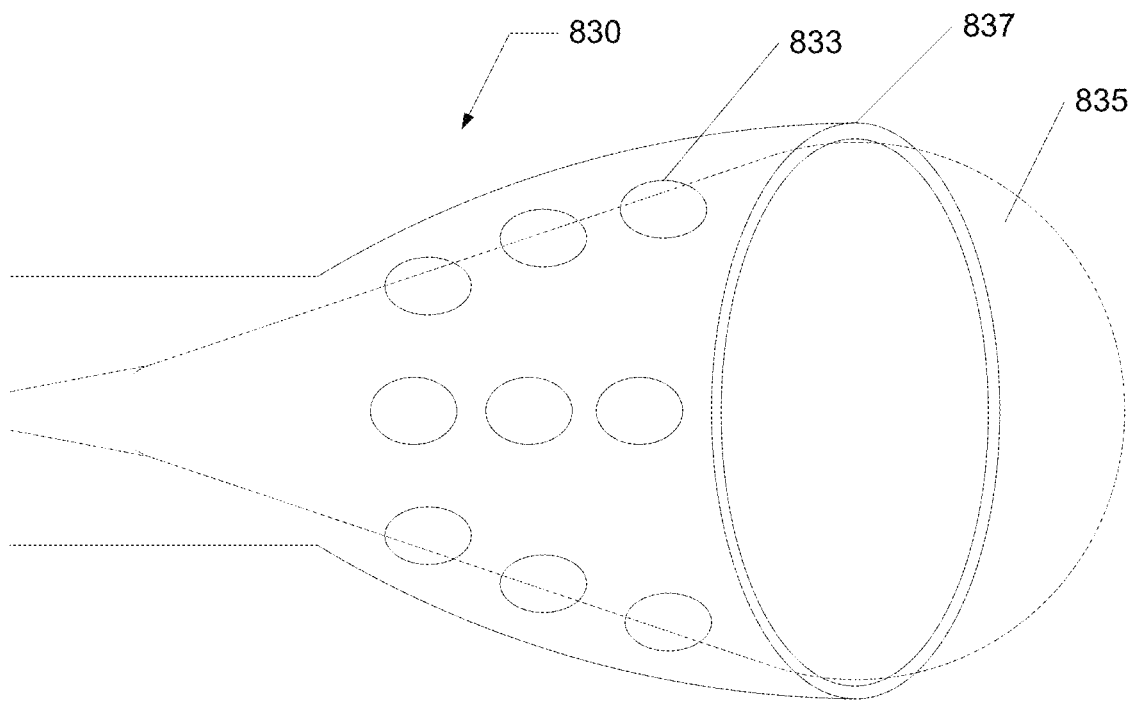
FIG. 8B shows a catheter device with an inflatable balloon expanding the tip of the catheter device.

FIG. 8B illustrates a variation of a catheter device shown in FIG. 8A. Shown in FIG. 8B is a catheter device 830 that has multiple optical fibers where distal ends 833 of the optical fibers are located at a peripheral surface of the catheter device at its tip. In this implementation, the catheter device also includes an inflatable balloon 835 which can be expanded by injecting air or other gas from its proximal end (now shown). Outer sheath 837 at the tip of the catheter device is elastic so that when the balloon expands, the outer sheathing at the tip of the catheter device expands as well.

The catheter devices shown in FIGS. 8A and 8B are particularly useful in measuring oxygen saturation level of a tubular organ such as the intestine. The tip of the catheter device can be expanded by a balloon so that multiple sensor openings at the tip of the catheter device can contact an interior wall of the intestine. Thus, multiple optical measurements can be made simultaneously. By adjusting an amount of fluid (gas or liquid) in the balloon, the tip of the catheter device can be expanded sufficiently so that distal ends of the optical fibers can contact a whole section of the intestinal wall.

The catheter devices described above are typically inserted into the mouth or anus and is guided down to a body cavity (e.g., intestine) to make oxygen saturation measurements of a desired area. The catheter devices can be guided to a desired location in the body by a number of different ways.

In one implementation, the optical fibers in the sensor probe can serve a dual function—measuring tissue oxygen saturation, as well as illuminating and viewing the tissue. As described above, a sensor probe tip contacts a tissue and transmits a near infrared light or visible light having a wavelength between about 600 nanometers to about 900 nanometers to measure oxygen saturation value of the tissue. To view the tissue, the tip of the sensor probe can be kept some distance away from the tissue (without contacting the tissue) so that light from the sensor probe can illuminate the tissue.

To illuminate the tissue using the sensor probe, any suitable wavelengths of light can be used. For example, the signal emitter which is connected to the sensor probe can generate the same wavelengths of light for measuring oxygen saturation of a tissue and to illuminate and view the tissue.

Alternatively, the signal emitter can generate different wavelengths of light, for example a broad band of white light in a visible spectrum, to obtain an image of the tissue. In this implementation, visible light can be used to guide the sensor probe to a desired location of the intestine. When the sensor probe reaches the desired location, the visible light can be turned off and the signal emitter can switch to light in an infrared spectrum to make oxygen saturation measurements.

In another implementation, the catheter devices can be guided inside the patient's body by using a separate imaging device. For example, the catheter devices can be viewed inside the patient's body with an aid of an ultrasound device, X-ray device, CT scan, MRI scan, PET scan or others. With an assistance of these imaging devices, the tip of the catheter device can be guided to a desired location in the intestine to make oxygen saturation measurements.

In yet another implementation, the catheter device or sensor probe (without an outer sheath) can be incorporated into a conventional endoscopic device. A conventional endoscopic device typically includes an elongated shaft which can be inserted into a body cavity, a light delivering element to illuminate an internal tissue, and an image detecting element transmitting the image of the tissue back to a viewer. Thus, by combining a sensor probe (or catheter device) of the present invention with a conventional endoscopic device, the doctor can view the tissue while measuring oxygen saturation of the tissue using the sensor probe.

FIG. 9A shows a schematic diagram of a system that includes an endoscopic device 910 into which a sensor probe 913 is incorporated. Endoscopic device 910 has a control head 915 and an elongated shaft 917 which are connected together. Control head 915 also connects elements in the elongated shaft to a light source 921 and an image monitor 923 by a cord 925. Sensor probe 913 is connected to a console 931 by a cable 933.

Elongated shaft 917 contains a light delivering element 951 (shown in FIG. 9B) that provides light to illuminate a tissue to be examined. The light delivering element typically includes a fiber optic bundle that is connected to an external light source 921 by a cord 925. The light bundles run uninterruptedly from the tip of the elongated shaft through cord 925 directly to light source 921. The image of the tissue is picked up at an image detecting element 955 (shown in FIG. 9B). The image detecting element typically includes a coherent fiber optic bundle which transfers the image to an eyepiece 927. Alternatively, the image can be transferred to a camera which sends signals via cord 925 to image monitor 923, where the doctor can view the tissue on a monitor screen.

Control head 915 controls functions of several components. For example, the control head can contain a deflection control 919 which allows remote control of the tip of elongated shaft 917, in order to maneuver it and guide it through body cavities. The tip portion of the elongated shaft 917 may be bendable by deflection control 919 to get a clearer view of the area to be observed. The control head can also contain a control button for gas 945 and a control button for suction 947 which can be used to clear damaged tissue and other debris around the tip of the elongated shaft.

The control head can also include one or more ports 949 for an instrument channel which runs along the longitudinal axis of elongated shaft 917. The instrument channel in an endoscopic device is typically between about 2 millimeters to about 6 millimeters, more typically between about 2 millimeters to about 4 millimeters, in diameter. The instrument channel can be used to insert any thin, flexible tools such as biopsy forceps, needles, and other tools through the elongated shaft and into the field of view during a surgical procedure.

In one implementation of the invention, sensor probe 913 can be incorporated into the instrument channel of an endoscopic device as shown in FIGS. 9A and 9B. The endoscopic device can have an additional instrument channel so that another tool, such as a biopsy needle, can be inserted into the channel and a biopsy of a tissue sample can be obtained during an examination.

FIG. 9B illustrates a detail view of a tip of elongated shaft 917 shown in FIG. 9A. Sensor probe 913 can be manipulated at its proximal end near port 949 (shown in FIG. 9A) by hand or robotically so that it can be extended beyond the distal end surface of the elongated shaft. In sensor probe 913, there are two optical fibers 961 and 963. One optical fiber can be used to emit light into a tissue, and the other optical fiber can be used to detect an attenuated version of the light that has reflected from the tissue. The extension of the sensor probe beyond the distal end surface of the elongated shaft may allow a doctor to clearly view the tissue while taking oxygen saturation measurements of the tissue.

Alternatively, the sensor probe may be affixed at and flushed with the distal end surface of the elongated shaft of an endoscopic device. Rather than manipulating the sensor probe itself, the tip of the elongated shaft of the endoscopic device can be maneuvered by deflection control 919 so that the tip of the elongated shaft can be bent and contact a tissue at a desired location.

While FIGS. 9A and 9B illustrate an embodiment where a sensor probe is incorporated into an instrument channel of an endoscopic device, a sensor probe can be located elsewhere. For example, a sensor probe can run along parallel to the elongated shaft of an endoscopic device. The sensor probe can be affixed to an outer surface of the elongated shaft by a shrink wrap tubing or by other fastener.

Embodiments shown in FIGS. 9A and 9B have advantages in that a sensor probe is combined with an endoscopic device that has a built-in light delivering element and an image detecting element for viewing a tissue. Thus, the use of an additional imaging device is not necessary to view the tissue. Further, an additional instrument channel present in the endoscopic device allows a doctor to take a biopsy of a tissue sample or to treat the tissue when the sensor probe measurements indicate anomaly in the tissue.

In another aspect of the invention, a device includes a marking mechanism near a tip of a sensor probe. The marking mechanism includes a feature that allows a doctor to mark or place a visible trace on a tissue. When sensor probe measurements indicate that a particular area of the intestine or mesentery has an oxygen saturation value substantially lower than a normal range, then it may be desirable to mark the area using the marking mechanism. The markings provide a visual indicator for the doctor for a subsequent treatment or operation.

Figure 10A:
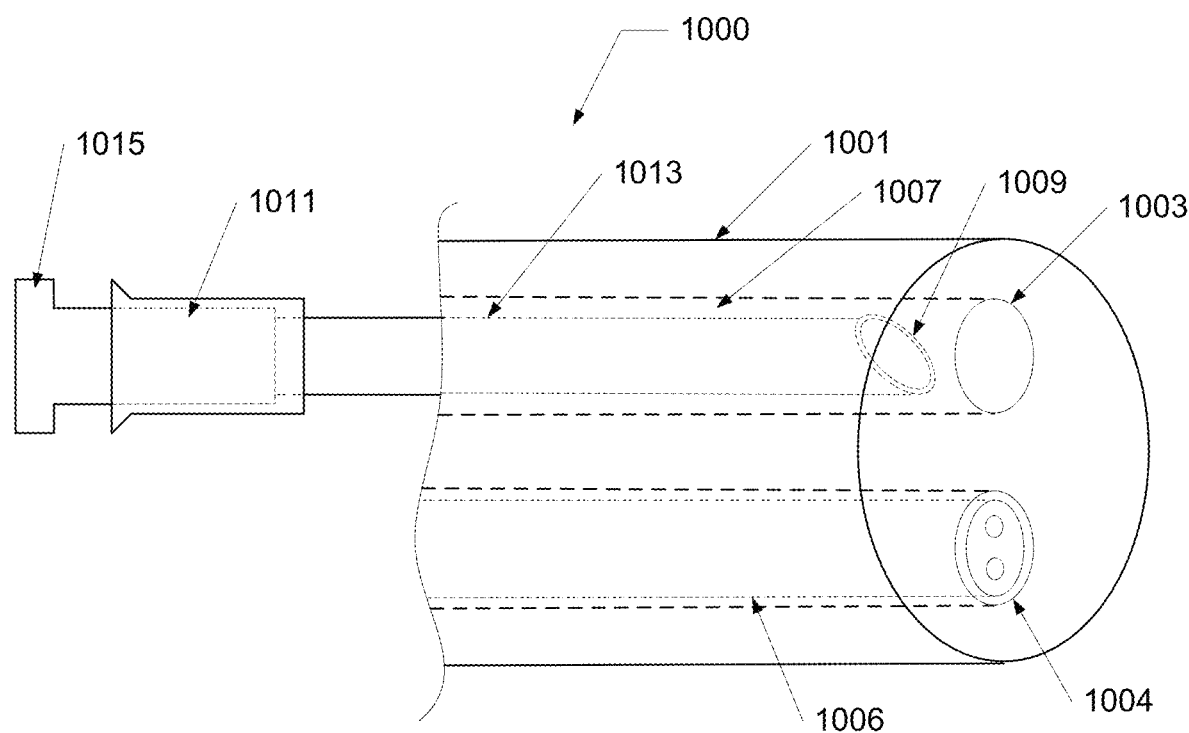
FIG. 10A shows a catheter device that includes a marking mechanism.

FIG. 10A illustrates an embodiment of a catheter device 1000 that includes an elongated tube 1001, such as a catheter, with two lumens 1003 and 1004. A sensor probe 1006 is disposed inside lumen 1004. A marking mechanism 1007 is disposed in lumen 1003 of the catheter device. A middle portion of the catheter device is omitted in FIG. 10A, and a proximal end of the catheter device is shown on the left hand side of FIG. 10A. The catheter device in embodiments of the invention allows the doctor to make oxygen saturation of a tissue at the same time as marking the tissue as necessary or desired.

In one implementation, marking mechanism 1007 can include an injection needle. As shown in FIG. 10A, the marking mechanism has a long cannula 1013 with a beveled needle 1009 at its distal end so that the needle can puncture and tattoo a tissue. The marking apparatus also has a housing 1011 which is connected to a proximal end of cannula 1013, and the housing holds a marking agent. The marking agent stored in the housing can be released into beveled needle 1009 by pushing onto a plunger 1015.

Any suitable marker that is compatible with a human body can be used in embodiments of the invention. In one embodiment, a marker is a biocompatible dye or ink. For example, a marker can be india ink, methylene blue, boluidine blue, congo red, or others. India ink provides a permanent marking for a bowel tissue. Thus, india ink can be used during an exploratory procedure so that marking can be viewed during a subsequent surgery. Alternatively, methylene blue can be used to mark a tissue during an operation, as it provides a temporary marking of a bowel tissue.

In another embodiment, a marker can be a solid marker. For example, a marker can be magnetic particles which can be tattooed or injected into a tissue. A tissue marked with magnetic particles can be localized in a subsequent surgery by using a magnetic or ultrasound detector.

Figure 10B:
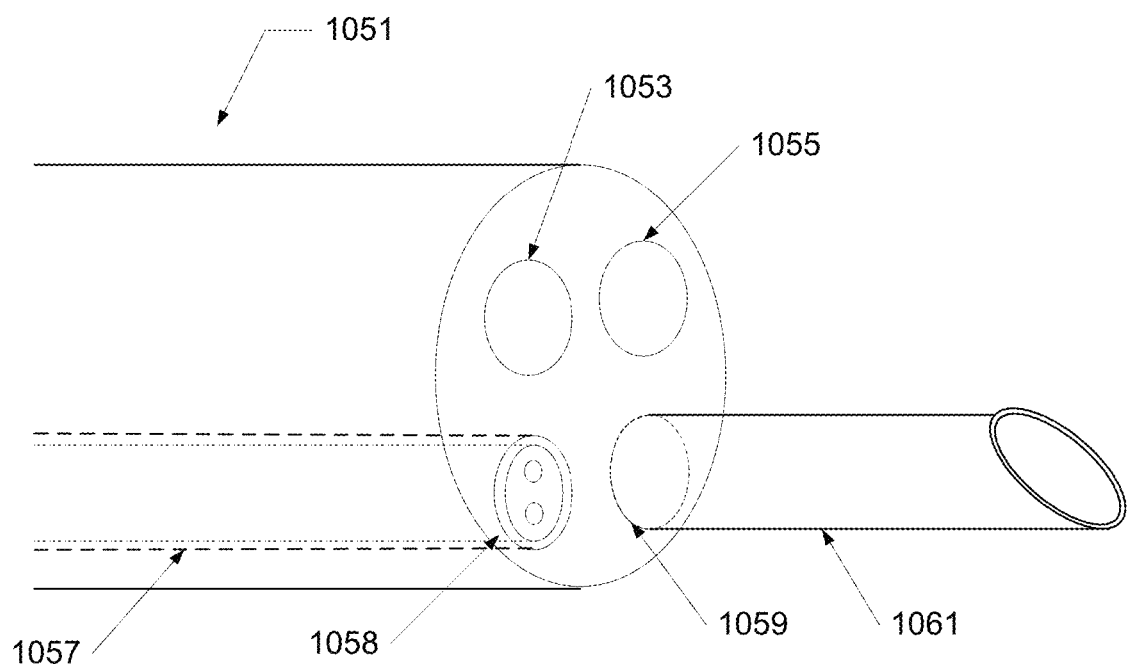
FIG. 10B shows an endoscopic device that includes a marking mechanism.

In another implementation, a marking mechanism is incorporated into an extra instrument channel of an endoscopic device. FIG. 10B illustrates a distal end of an elongated shaft of an endoscopic device. An elongated shaft 1051 of an endoscopic device has a light delivering element 1053 and an image detecting element 1055. The elongated shaft of the endoscopic device also includes two channels 1057 and 1059 along its longitudinal axis. Channel 1057 includes a sensor probe 1058 having an oximeter sensor at its tip. Channel 1079 includes a marking mechanism 1061.

A marking mechanism can be made of any suitable instruments. For example, these include a sclerotherapy needle, an injection syringe, or others. When the elongated shaft of the endoscopic device travels inside the intestine, the distal end of the marking mechanism remains in channel 1059 to avoid accidental puncture of the intestine. When the doctor desires to mark a tissue, a beveled needle end of the marking mechanism is extended beyond the distal end of the elongated shaft. The beveled needle end of the marking mechanism can spray, tattoo, or inject a tissue with a marking agent.

While FIGS. 10A and 10B illustrate the use of a beveled needle to apply a marking agent to a tissue, other types of devices can be used as a marking mechanism. For example, rather than having a beveled needle to mark a tissue, the marking mechanism may include a sponge tip, a felt tip, or a ball-pen-like output end to apply a dye or ink onto a tissue.

The implementations discussed so far are used by introducing the device through a natural orifice of the body—such as the mouth or anus—to measure oxygen saturation of a mucosal surface (i.e., inner surface) of the intestine, or other body cavities. To measure oxygen saturation of a serosal surface (i.e., outer surface) of the intestine or mesentery, the catheter devices and endoscopic devices described above can be introduced into an abdominal cavity using a trocar or other incision apparatus. However, incisions in the abdominal tissue can lead to complications such as infection, adhesion of tissues underlying the incision, and hernia.

In another aspect, embodiments of the invention provide a device that can be introduced into an abdominal cavity with a small pin size hole in an outer tissue (e.g., abdominal skin and underlying connective tissues). Such device can be used to make oxygen saturation measurements of a serosal surface of the intestine or mesentery. Since no incision is required for this device, the use of the device will result in minimal discomfort, and reduced healing time and less medical complications for the patient.

Figure 11A:
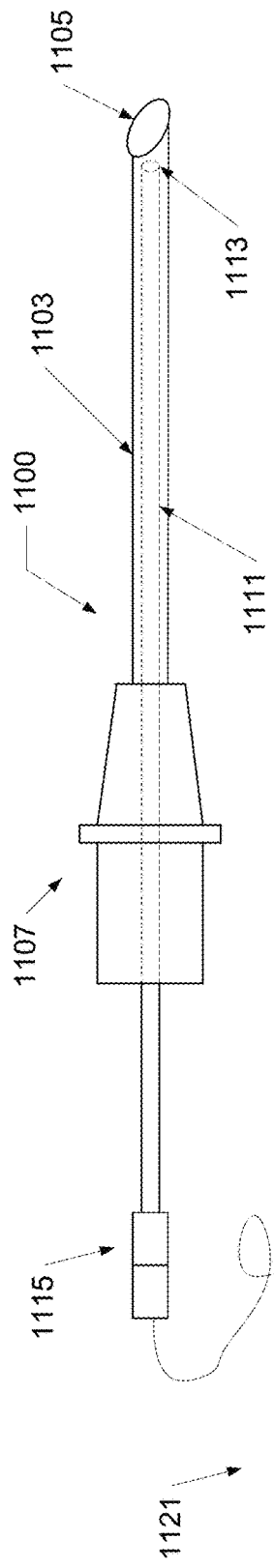
FIG. 11A shows a system that includes a needle sensor device that has a hollow needle with a beveled edge and a sensor probe disposed inside the hollow needle.

FIG. 11A shows a needle sensor device 1100 which can be introduced inside the body through the skin, rather than through natural orifices of the body to make oxygen saturation measurements of internal tissues, such as a serosal surface of the intestine or mesentery. The needle sensor device includes a hollow needle 1103 with a beveled edge 1105 at its distal end and a needle hub 1107. The needle sensor device further includes a sensor probe 1111 which is disposed inside hollow needle 1103. An oximeter sensor 1113 at a distal end of the sensor probe is located near beveled edge 1105. A proximal end of the sensor probe has a connector 1115, which connects the sensor probe to a monitoring console 1121 via a cable.

Figure 11B:
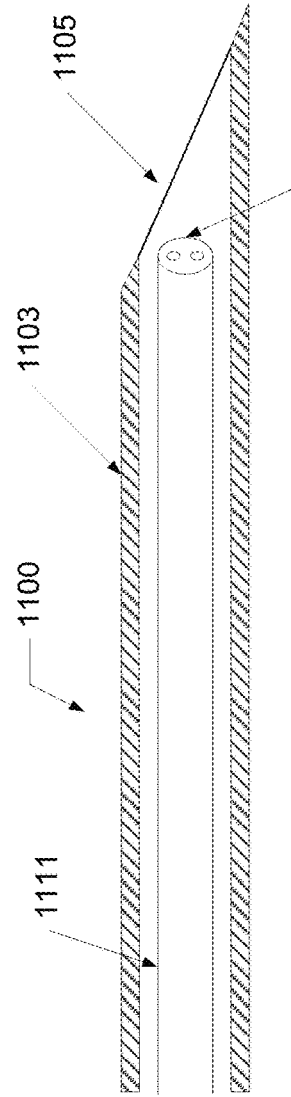
FIG. 11B shows a distal end of the hollow needle shown in FIG. 11A where the tip of the sensor probe is disposed inside the hollow needle.

FIG. 11B shows a more detailed view of a distal end of the needle sensor device shown in FIG. 11A. A distal end of needle sensor device 1100 has hollow needle 1103 with a beveled edge 1105. Oximeter sensor 1113 at a distal end of the sensor probe is located near the beveled edge of the hollow needle. Typically, the device as shown in FIG. 11B (with the sensor probe disposed inside the hollow needle) is used to puncture an outer tissue and to introduce the device inside the body.

Figure 11C:
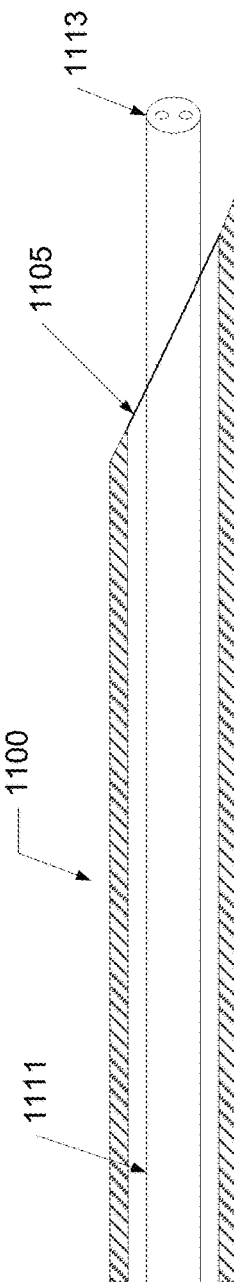
FIG. 11C shows a distal end of the hollow needle shown in FIG. 11A where the tip of the sensor probe is extended beyond a distal end of the hollow needle.

FIG. 11C shows another view of a distal end of needle sensor device 1100. As shown in FIG. 11C, oximeter sensor 1113 at a distal end of the sensor probe is extended beyond the beveled edge of the needle sensor device. The sensor probe fits snugly inside the hollow needle, and it can be manipulated from its proximal end to slide back and forth inside the hollow needle. Once the hollow needle is introduced inside the body, the sensor probe can be extended beyond the beveled edge of the needle sensor device to make contact with a tissue where oxygen saturation measurements are desired.

The hollow needle can be made of any suitable material, such as surgical grade stainless steel, titanium, aluminum, plastics, ceramics, composites, or others. The needle hub can be made of the same material as the hollow needle or of a different material. For example, the needle hub may be made of plastics while the hollow needle is made of stainless steel for a needle sensor device.

While the needle sensor device shown in FIG. 11A includes a needle hub which makes it convenient for the doctor to hold the device and introduce the hollow needle into a body, the device does not necessarily have to include the needle hub. Rather, the needle sensor device may only include a hollow needle and a sensor probe. The shape of a hollow needle can be derived from any suitable needle, such as a biopsy needle, core biopsy needle, phiebotomy needle, spinal tap needle, Verres needle, or others.

The dimension of a hollow needle used in a needle sensor device can vary depending on its application. It is desired that the hollow needle has a small diameter of about 5 millimeters or less, more typically about 4 millimeters or less, even more typically about 3, 2, 1, 0.5 millimeters or less. The length of the hollow needle can also vary, typically from about 5 centimeters to about 40 centimeters, depending on the depth of a tissue that the doctor desires to reach inside the body.

In another aspect of the invention, a needle sensor device can be used in combination with a trocar. A trocar is a hollow cylinder with a sharply pointed end that is used to introduce cannulas and other similar implements into body cavities. The cannula contained in the trocar is inserted through the skin to access a body cavity in which laparoscopic or other type of surgery is to be performed. The trocar often functions as a portal for the subsequent placement of other instruments for surgery.

Although the needle sensor device can be used alone to puncture an outer tissue (e.g., skin, abdominal wall, and others) and to introduce a sensor probe inside the abdomen to measure oxygen saturation of the intestinal or mesentery tissue, a trocar can also be used to puncture the outer tissue, particularly when the outer tissue is too thick for the needle sensor device to puncture through. Then a needle sensor device (or a catheter device in accordance with the present invention) can be introduced into the abdominal space through the trocar. Furthermore, the trocar can be used as a portal to place other surgical instruments into the abdomen.

Figure 11D:
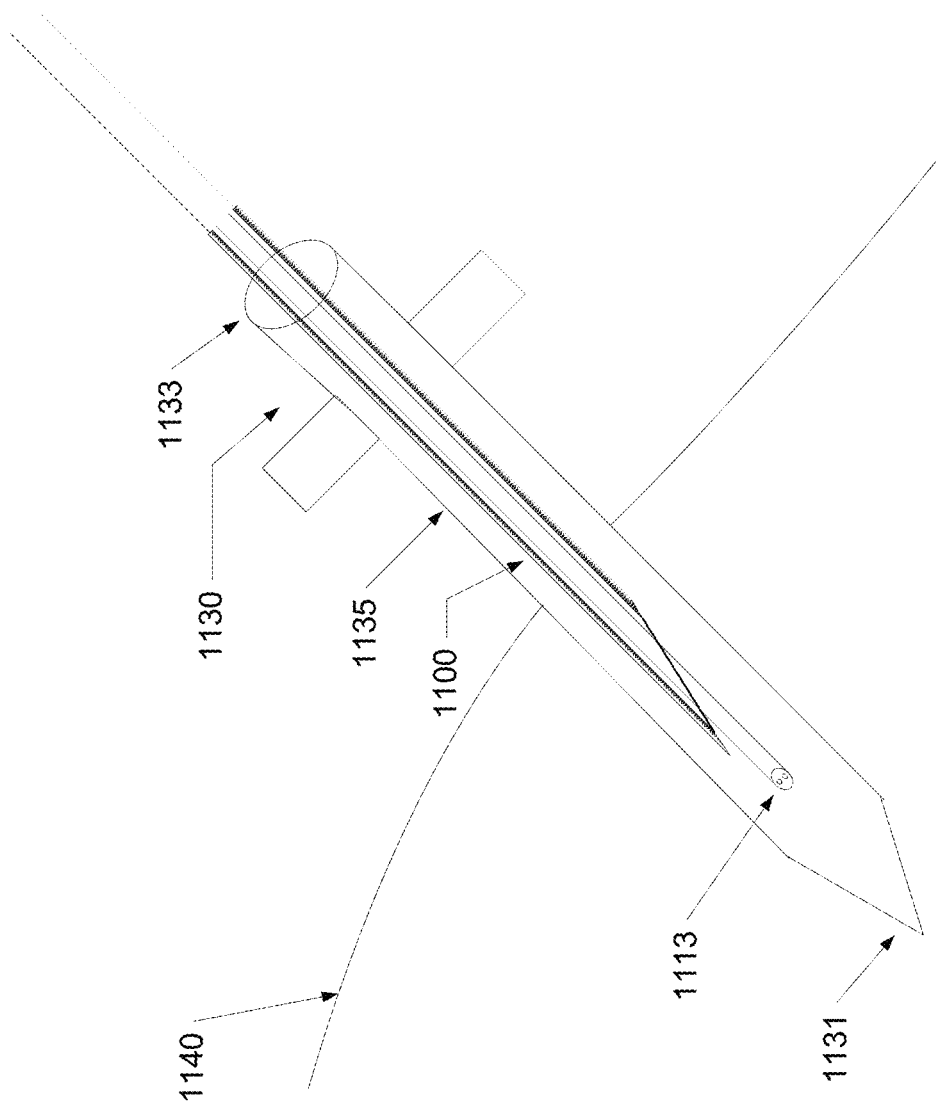
FIG. 11D shows the use of a trocar in combination with a needle sensor device to introduce a sensor probe into an abdominal cavity.

FIG. 11D shows an embodiment where a trocar is used in combination with a needle sensor device. A trocar 1130 has a hollow tube or cannula 1135 with a pointed end 1131 which can be used to puncture an abdominal wall 1140. A proximal end 1133 of the trocar has an opening to introduce various instruments. As shown in FIG. 11D, a needle sensor device 1100 is introduced through the opening at the proximal end of the trocar. A sensor probe 1113 of the needle sensor device can be manipulated and pushed through the distal end of the trocar. Once the sensor probe is inside the abdominal cavity, it can contact and measure oxygen saturation of the intestinal or mesentery tissue.

The devices according to embodiments of the invention have many applications. For example, the devices can be applied in diagnosing intestinal ischemia in a patient by measuring oxygen saturation level of an intestinal tissue or mesentery. Furthermore, if oxygen saturation measurements indicate that an area in the intestine may not be viable, then the area can be marked with a marking mechanism for subsequent resection surgery. The devices can also be used to monitor an intestinal tissue that has gone through a surgical procedure to determine if the surgery was successful in removing a nonviable tissue and preserving a viable tissue.

In one implementation, the devices in accordance with the present invention can be used as a diagnostic tool for detecting intestinal ischemia in a patient. Symptoms of intestinal ischemia are broad and vague. There is no single set of symptoms which can fully predict the type of ischemic injury. Subsequently, intestinal ischemia is difficult to diagnose.

There are some common symptoms for different types of ischemia. The most common form of ischemic injury to the intestine is colon ischemia. Colon ischemia usually results in sudden, mild-to-moderate left-sided abdominal pain with an urgent desire to defecate. Also, the patient typically passes bright red or maroon colored blood mixed with the stool within 24 hours after the onset of the abdominal pain.

Another type of ischemia is an acute episode of small intestinal ischemia which typically begins with the sudden onset of severe abdominal pain. Early in the process, the abdomen is usually soft, flat, and not tender to touch. Also, an abdomen may also be distended. If small intestinal ischemia is caused by an acute arterial occlusion caused by an embolus, then the patient may suffer a sudden, forceful bowel movement associated with severe abdominal pain.

Another type of small intestinal ischemia is caused by an arterial or vein obstruction due to thrombus. This type of intestinal ischemia develops more slowly over weeks to months. Typically, it begins with abdominal pain after meals, weight loss, and a change of bowel habits. Other symptoms may include nausea, vomiting, and diarrhea with or without blood.

Chronic small intestinal ischemia is typically associated with dull, cramping abdominal pain felt 10 to 30 minutes after eating and reaches its peak 1 to 3 hours after a meal. The pain can increase in severity to the point where the patient fears eating and exhibits a severe weight loss.

When a patient presents some of the symptoms described above, it is difficult for the doctor to determine if the symptoms are due to intestinal ischemia or other unrelated conditions. A doctor typically considers the patient's medical history, symptoms, and physical exam, followed by imaging tests such as ultrasound, X-ray, CT scan, or Mill scan to help determine if the symptoms are related to intestinal ischemia.

If blockage of mesenteric blood vessels is suspected, the doctor may order angiography, a special X-ray study of the blood vessels. While angiography may be helpful in determining if blockage in mesenteric blood vessels is causing intestinal ischemia, other types of intestinal ischemia (e.g., chronic small intestinal ischemia, nonocclusive acute small intestinal ischemia, and others) are difficult to diagnose.

Since the devices according embodiments of the invention directly assess the oxygenation state of the intestine and mesentery, the devices provide a better diagnostic tool in determining whether a patient is suffering from intestinal ischemia due to poor oxygenation of the intestinal tissue or mesentery. Thus, the doctors can use embodiments of the invention to determine if the patient's symptoms are directly related to an ischemic condition of the intestine or mesentery.

Figure 12:
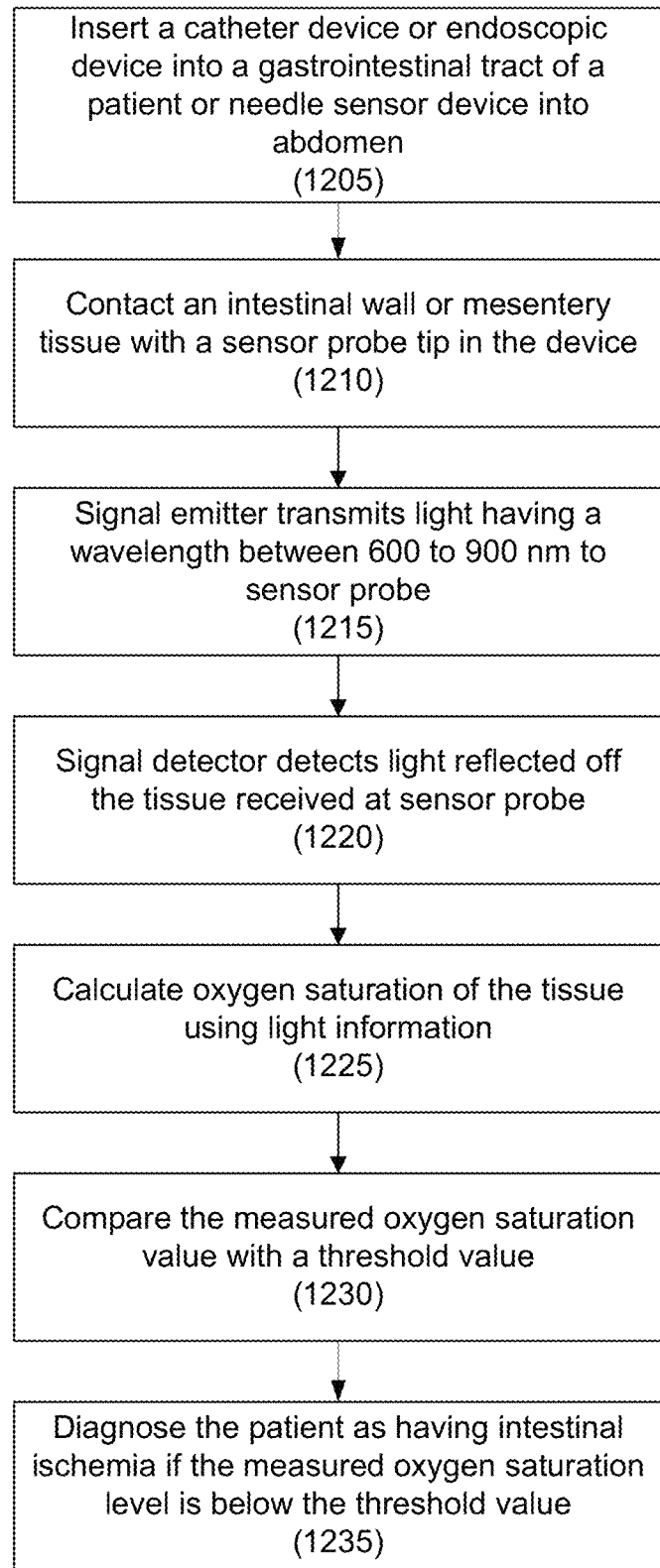
FIG. 12 shows a flow diagram for operating a catheter device, endoscopic device, or needle sensor device in measuring oxygen saturation of the intestine or mesentery.

FIG. 12 is a flow diagram that shows a method of measuring oxygen saturation level of the intestine or mesentery using a device in accordance with the present invention and determining if the patient suffers from intestinal ischemia.

A specific flow is presented, but it should be understood that the invention is not limited to the specific flows and steps presented. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data.

First, in a step 1205, to measure oxygen saturation values of a mucosal surface of the intestine, a doctor inserts a catheter device or endoscopic device into a gastrointestinal tract of a patient, either through the mouth or anus. Alternatively, to measure oxygen saturation values of a serosal surface of the intestine or mesentery, the doctor punctures an outer tissue (e.g., skin) with a needle sensor device into an abdominal cavity. The device can be guided inside the body cavity with an aid of ultrasound, MRI, or light delivering element of the endoscopic device as described above.

In a step 1210, when the tip of the device reaches a desired location in the intestine or mesentery, the sensor probe at the tip of the device can be manipulated to contact a target tissue. When the sensor probe makes a proper contact with the target tissue, then the computer which is connected to the sensor probe via optical fibers will indicate that the signal quality factor is acceptable or within a normal range.

In a step 1215, once the tip of the sensor probe makes a proper contact with the target tissue, a computer (e.g., console) directs a signal emitter (connected to the sensor probe and the computer) to transmit light to the sensor probe, and into the target tissue. After the light is transmitted into the tissue, some of the light is reflected off of the tissue. Typically, the signal emitter transmits light having a wavelength between about 600 nanometers to about 900 nanometers. In a specific implementation, the signal emitter transmits an optical signal having two or more different wavelengths to be transmitted through the sensor probe, where a first wavelength is about 690 nanometers, and a second wavelength is about 830 nanometers.

In a step 1220, a detector (connected to the sensor probe and the computer) detects the light reflected off of the target tissue. The detector then sends this light information to the computer.

In a step 1225, the computer calculates the oxygen saturation of the target tissue using this light information.

In a step 1230, the computer calculates the measured oxygen saturation of the target tissue with a threshold value.

A normal range of oxygen saturation for the intestine or mesentery may vary between about 60 and 90 percent. Thus, a threshold value for determining if a region in the intestine is suffering from ischemia may be set at 60 percent or below. For example, the threshold value may be set at 59, 55, 50, 45, 40, 35, 30, 25, 20, 15, 10, 5, 0 percent, or any other numbers in this range. The threshold value can vary depending on which region of the intestine was tested for oxygen saturation level. Accordingly, depending on the intestinal region being tested or other factors, the threshold value may be set at a different level.

The steps shown in FIG. 12 can be repeated after moving the sensor probe to different locations in the intestine or mesentery.

In a step 1235, if the patient presents various symptoms described above and if the oxygen saturation measurements from one or more regions of the patient's intestine or mesentery are lower than a threshold value, then a patient can be diagnosed as having intestinal ischemia. Since embodiments of the invention directly assess the oxygenation state of the intestine and mesentery, the doctor can make a more definitive diagnosis of intestinal ischemia in a patient.

The flow diagram shown in FIG. 12 can also be applied in monitoring oxygen saturation level of the intestine or mesentery during a surgical procedure. If symptoms of intestinal ischemia are severe in a patient and the doctor suspects that a portion of the intestine is infracted (dead), the doctor may decide to perform a resection of a dead tissue followed by an anastomosis. In determining which intestinal tissue may be viable or nonviable, the doctor can use the devices of the present invention, rather than relying on subjective criteria such as color of the intestine.

In determining which intestinal tissue is viable or nonviable during a surgery, the doctor can follow steps 1210 through 1230 in the flow diagram provided in FIG. 12. As stated above, the threshold value for viability of a tissue may differ depending on tissue type, age of the patient, or the patients' medical history. For example, a threshold value for viability of the colon may be selected at 40 percent oxygen saturation level, where a threshold value for viability of the small intestine may be selected at 35 percent oxygen saturation level.

Furthermore, the flow diagram shown in FIG. 12 can be used to monitor oxygen saturation level of the intestine or mesentery after surgery or other treatment. Even after an anastomosis procedure, there is a risk that rejoined portions of the intestine may fail if there is too much strain or limited vascular supply to the rejoined portions. Since the devices of the present invention can monitor the oxygenation state of the intestine noninvasively, they can be applied to determine if the joined portions of the intestine are adequately oxygenated and healthy.

In another aspect of the invention, the method in accordance with the present invention includes marking a portion in the intestine or mesentery after a sensor probe makes oxygen saturation measurements. Prior to a surgical procedure, the doctor may desire to notate a portion of the intestine that is viable or nonviable based on oxygen saturation measurements of the tissue. The devices with a marking mechanism in accordance with the present invention can be used to mark either viable or nonviable portions of the intestine prior to a resection procedure. By clearly marking the tissue prior to or during the surgery, the doctor can clearly view which portion of the intestine needs to be resected or treated.

Figure 13:
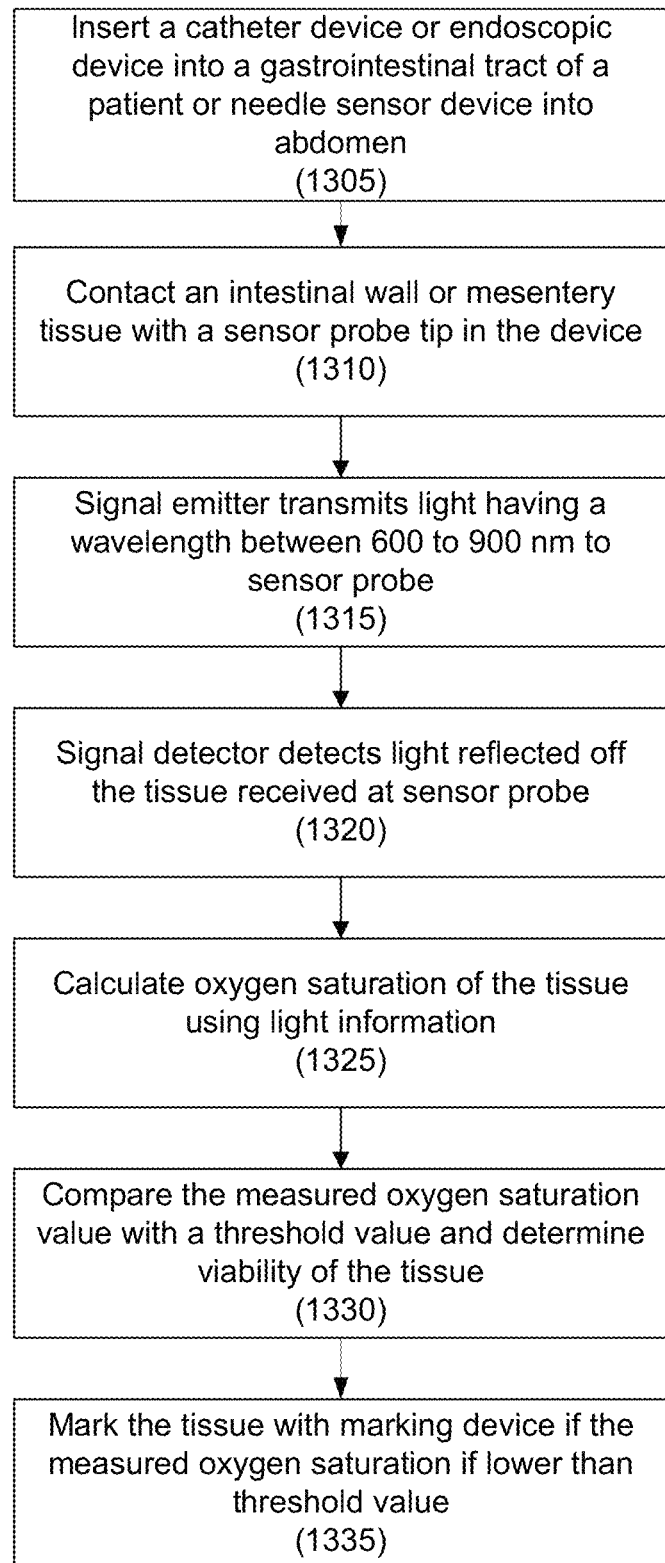
FIG. 13 shows a flow diagram of operating a catheter device, endoscopic device, or needle sensor device and marking a tissue of the intestine or mesentery with a marking mechanism.

FIG. 13 is a flow diagram that shows a method of measuring oxygen saturation level of a tissue in the intestine or mesentery using a device with a marking mechanism in accordance with the present invention. The steps in FIG. 13 can be followed to mark a portion of the intestine or mesentery that has a poor oxygen saturation level, which may be indicative of infarction of the tissue. Most of the steps shown in FIG. 13 are similar to those shown in FIG. 12.

First, in a step 1305, to measure oxygen saturation values of mucosal surface of the intestine, a doctor inserts a catheter device or endoscopic device into a gastrointestinal tract of a patient, either through the mouth or anus. Alternatively, to measure oxygen saturation values of a serosal surface of the intestine or mesentery, the doctor punctures an outer tissue (e.g., skin) with a needle sensor device into an abdominal cavity. Typically, the device is guided inside the body cavity with an aid of ultrasound, MRI, or image detecting element of the endoscopic device as described above.

In a step 1310, when the tip of the device reaches a desired location in the intestine or mesentery, the sensor probe at the tip of the device can be manipulated to contact a target tissue.

In a step 1315, once the tip of the sensor probe makes a proper contact with the target tissue, a computer (e.g., console) directs a signal emitter (connected to the sensor probe and the computer) to transmit light to the sensor probe, and into the target tissue. After the light is transmitted into the tissue, some of the light is reflected off of the tissue.

In a step 1320, a detector (connected to the sensor probe and the computer) detects the light reflected off of the target tissue. The detector then sends this light information to the computer.

In a step 1325, the computer calculates the oxygen saturation of the target tissue using this light information.

In a step 1330, the computer calculates the measured oxygen saturation of the target tissue and compares it with a threshold value. The threshold value may vary depending on many factors. As noted above, a normal range of oxygen saturation level may vary depending on the intestinal region from which oxygen saturation measurements are made. However, if the oxygen saturation value of an intestinal tissue is substantially lower than the normal range, then it may be considered that the tissue is not viable. For example, the threshold value of nonviability of a tissue may be set at 59, 55, 50, 45, 40, 35, 30, 25, 20, 15, 10, 5, 0 percent, or any other number in the range by the doctor.

Once it is determined that the measured oxygen saturation value of the target tissue is lower than the threshold value, then the target tissue is marked with a marking mechanism. As described above, the tissue can be marked with an ink or dye (e.g., india ink) or solid particles (e.g., magnetic particles). The markings on the tissue provide a clear visual indicator for the doctor when the patient goes through a subsequent surgery or treatment.

In another aspect of the invention, the effects of a temporary induced ischemia on intestinal or mesentery tissue oxygen saturation can be analyzed to determine if a patient is suffering from intestinal ischemia. A temporary ischemic period can be induced on an intestinal or mesentery tissue by using a device that constricts a mesenteric artery. Since the tissue continues to consume remaining oxygen from blood (with no or little influx of fresh arterial blood), tissue oxygen saturation will decline gradually during the temporary ischemic period. If the tissue is healthy and normal, then stopping or reducing the blood flow to the tissue will result in a significant reduction of measured oxygen saturation over time. If the intestinal or mesentery tissue already suffers from ischemia (e.g., due to clogged mesenteric arteries or infarct intestinal tissue), then stopping or reducing the arterial blood flow will not significantly reduce measured oxygen saturation of the tissue.

FIGS. 14A through 14E illustrate methods for determining which portion of the large intestine suffers from intestinal ischemia by inducing a temporary ischemia. The figures also illustrate how oxygen saturation measurements during the temporary induced ischemic period can be used during resection and anastomosis procedures.

Figure 14A:
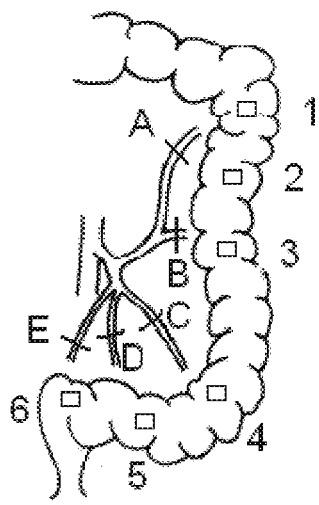
FIG. 14A shows a large intestine and mesenteric arteries labeled A through E which supply blood to the large intestine, where the mesenteric arteries are clipped to stop or reduce the blood flow to the large intestine to induce a temporary ischemia.

FIG. 14A shows five different mesenteric arteries labeled A, B, C, D, and E which supply blood to different portions of the large intestine labeled 1, 2, 3, 4, 5, and 6. One artery can supply more than one selected portion of the large intestine. As shown, a blood supply to the large intestine can be reduced or stopped by clipping one or more mesenteric arteries at a time or simultaneously. Clipping the mesenteric arteries can be achieved during an open abdominal surgery. Alternatively, a trocar can be used to introduce a device to constrict mesenteric arteries (e.g., clip). Other methods, such as pressing down on arteries, can be used to reduce or stop blood supply to the intestinal or mesentery tissue to induce a temporary ischemia. Any suitable oximeter devices (e.g., a catheter device, an endoscopic device, or a needle sensor device) can be used to measure oxygen saturation of the intestinal or mesentery tissue during the temporary induced ischemic period.

Figure 14B:
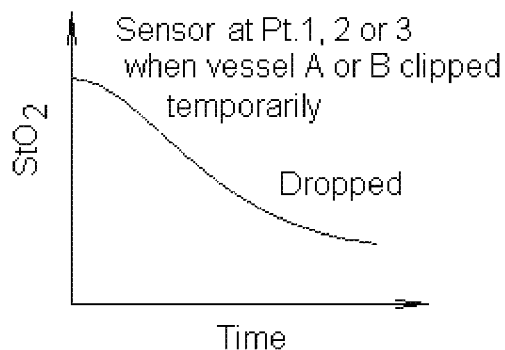
FIG. 14B shows changes in oxygen saturation level of a healthy large intestine tissue.

FIG. 14B shows oxygen saturation measurements from intestinal portions 1, 2, or 3 of the large intestine. Initially (at time 0), the tissue oxygen saturation level at portions 1, 2, or 3 is high. Once the mesenteric arteries A or B are clipped (which supply blood to portions 1, 2, and 3), the oxygen saturation levels of these portions decrease over a time period. This result indicates that intestinal portions 1, 2, and 3 are healthy and normal, and that they normally receive adequate blood supply from mesenteric arteries A and B.

Figure 14C:
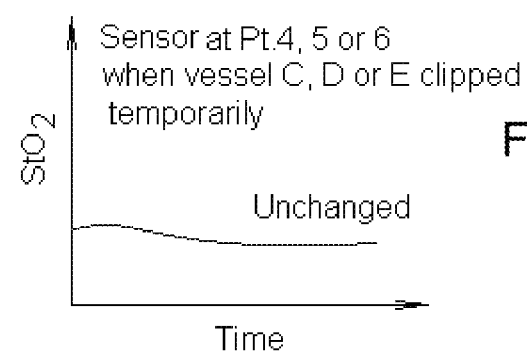
FIG. 14C shows changes in oxygen saturation level of a large intestine tissue which suffers from intestinal ischemia where a temporary induced ischemia does not affect the oxygen saturation of the tissue.

FIG. 14C shows oxygen saturation measurements from intestinal portions 4, 5, and 6. The initial value of tissue oxygen saturation level at these portions is low, when compared to the initial value for healthy intestinal portions 1, 2, and 3 shown in FIG. 14B. After clipping mesenteric arties C, D, or E (which supply blood to portions 4, 5, and 6), there is a minimal or no decrease of tissue oxygen saturation over a time period of induced ischemia. This result indicates that tissue portions 4 through 6 are already unhealthy or dead. Alternatively, mesenteric arteries C, D, and E are not adequately supplying blood to these portions because the arteries are clogged, inflamed, or diseased.

Figure 14D:
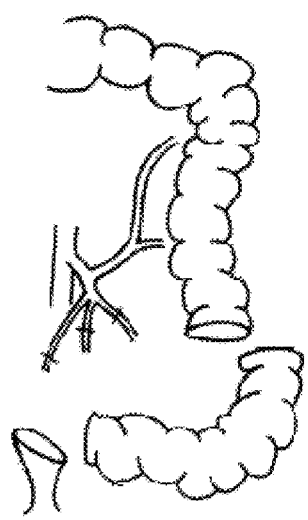
FIG. 14D shows a resection of an intestinal tissue which suffers from an intestinal ischemia.
Figure 14E:
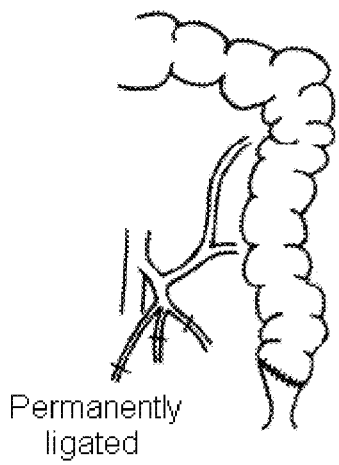
FIG. 14E shows an anastomosis procedure where a healthy portion of the large intestine is joined with the anus region.

Once it is determined that tissue portions 4, 5, and 6 are not viable, a resection of these portions of the large intestine can be performed as shown in FIG. 14D. Once the nonviable portion of the large intestine is resected, an anastomosis procedure can be performed by ligating a healthy end portion 3 with the anus region of the patient as shown in FIG. 14E. Once a nonviable portion of the large intestine is removed, the healthy portions of the large intestine can resume a normal function of the intestine after healing.

Figure 15:
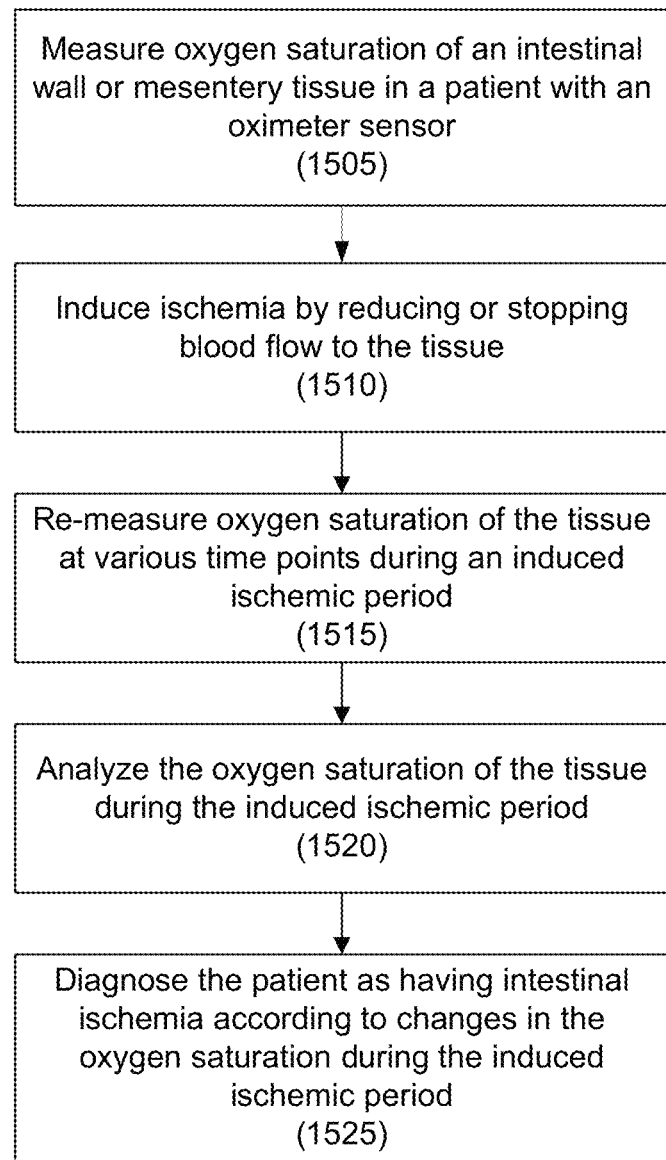
FIG. 15 shows a flow diagram for analyzing oxygen saturation changes of an intestinal or mesentery tissue during an induced ischemic period to determine if a patient is suffering from intestinal ischemia.

FIG. 15 shows a flow diagram for diagnosing intestinal ischemia in a patient by analyzing changes in oxygen saturation of an intestinal or mesentery tissue in a patient during a temporary induced ischemic period.

In a step 1505, oxygen saturation of an intestinal or mesentery tissue in a patient is measured with an oximeter sensor. Any suitable oximeter sensor can be used in this step to measure tissue oxygen saturation.

In a step 1510, an ischemia is induced in the intestinal or mesentery tissue by reducing or stopping the blood flow (e.g., by clipping or pressing down the mesenteric artery) to the tissue.

In a step 1515, oxygen saturation of the same portion of the tissue is remeasured with the oximeter sensor after specific time points after ischemia is induced.

In a step 1520, the changes in tissue oxygen saturation during the induced ischemic period are analyzed.

In a step 1525, the patient can be diagnosed as suffering from intestinal ischemia if changes in tissue oxygen saturation do not meet a threshold value.

In one embodiment, the analysis in step 1520 may include calculating a rate of change of oxygen saturation over a period of time. For example, a mesenteric artery supplying blood to the tissue can be clipped, and oxygen saturation of the tissue can be measured every 10 seconds, 30 seconds, one minute, two minutes, or other suitable time intervals. The blood supply to the tissue can be clipped for any suitable time period, as long as it does not negatively impact the patient's long-term health. For example, the blood supply can be clipped for a period anywhere between 1 minute, 2 minutes, 5 minutes, 10 minutes, 20 minutes, 30 minutes, or any other suitable time period. The measured oxygen saturation (e.g., in terms of percent) can be plotted against time. The rate of change can be calculated using any suitable method. For example, the rate of change can be measured and calculated around a midpoint of the induced ischemic period.

The rate of oxygen saturation change can be calculated, and compared to a threshold to determine whether the patient is suffering from intestinal or mesentery ischemia. A threshold can be set differently depending on various factors (e.g., the patient's age, health history, gender, and others). A threshold can be set at any suitable rate, e.g., at about 3, 5, 10, 20, 30, 40, 50, 60, 70, 80, 90, or 100 percent per minute. For example, if the threshold is set at a rate of 20 percent oxygen saturation change per minute and if the patient's rate of change is calculated to be about 5 percent oxygen saturation change per minute, then the patient is diagnosed as having intestinal ischemia.

In another embodiment, the analysis in step 1520 may include determining either an absolute change or relative change in oxygen saturation level of the intestinal or mesentery tissue. Any suitable time point can be selected for measuring oxygen saturation level. For example, oxygen saturation can be measured before clipping the blood supply. After the blood supply to the intestinal or mesentery tissue is clipped, oxygen saturation can be measured at a selected time point (e.g., 5 minutes, 10 minutes, 20 minutes, 30 minutes, and others). Then the change in oxygen saturation level of the tissue can be recorded.

For example, at time zero (before clipping the mesenteric artery), the oxygen saturation value of a tissue is measured at 80 percent. At 10 minute time point after the mesenteric artery is clipped, the oxygen saturation of the same tissue is measured at 20 percent. Then the absolute change of oxygen saturation value may be recorded as being 60 percent. Alternatively, the relative change of oxygen saturation value may be recorded as being 75 percent (i.e., (80−20)/80). A healthy intestinal or mesentery tissue will have a higher absolute or relative change in oxygen saturation value (e.g., above 40 percent), whereas an intestinal or mesentery tissue that already suffers from ischemia will have a lower absolute or relative change in oxygen saturation value (e.g., below 40 percent).

The change in oxygen saturation level at a specific time point can be compared to a threshold. For example, ten minutes into the induced ischemic period can be selected as a time point to calculate the absolute change in oxygen saturation level of the intestinal or mesentery tissue, and a threshold may be selected at 40 percent. If a patient's oxygen saturation level changed less than 40 percent at ten minute time point during the induced ischemic period, then the patient can be diagnosed as suffering from intestinal ischemia. If the patient's oxygen saturation level changed more than 40 percent at ten minute time point during the induced ischemic period, then the patient can be diagnosed as being normal and healthy.

In addition to using the flowchart shown in FIG. 15 as a diagnostic tool for intestinal ischemia, the steps shown in FIG. 15 can be repeated and applied to determine which portion of the intestine or mesentery is causing intestinal ischemia. As shown in FIG. 14A through 14E, different mesenteric arteries can be pressed down or clipped, and different portions of the intestine or mesentery can be tested for their oxygen saturation level. The results of oxygen saturation change at different portions of the intestine can be used for resection or anastomosis procedures.

Figure 16A:
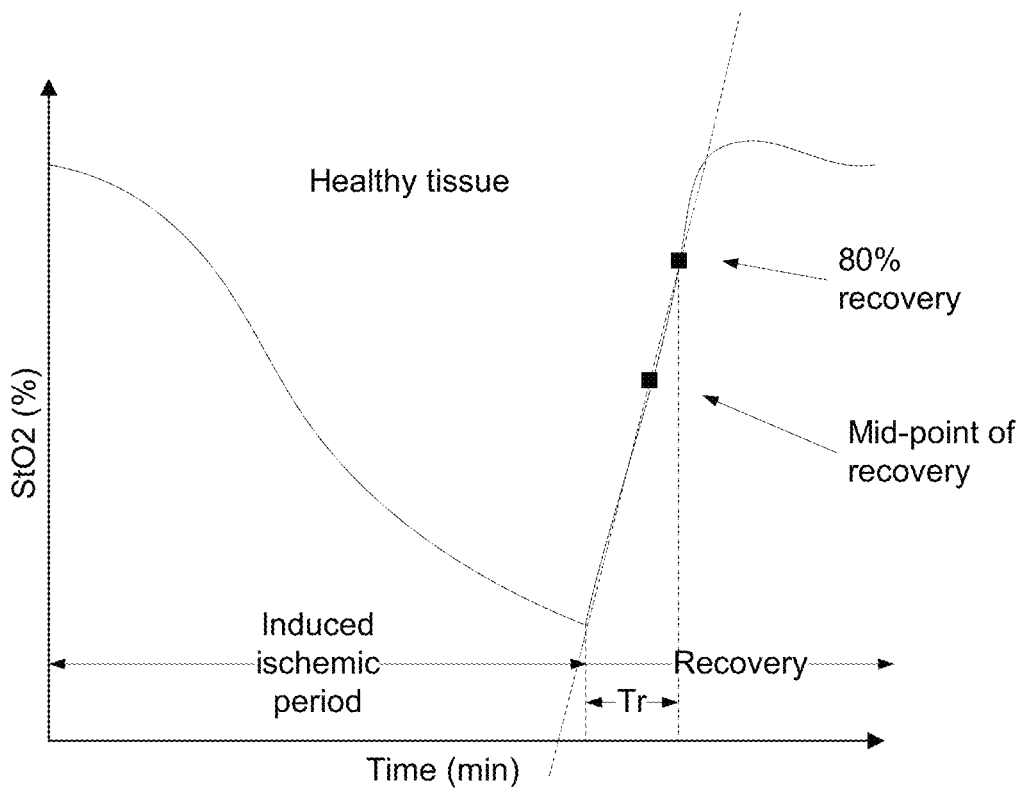
FIG. 16A shows a graph that shows oxygen saturation changes of a healthy intestinal or mesentery tissue during an induced ischemic period and during recovery.
Figure 16B:
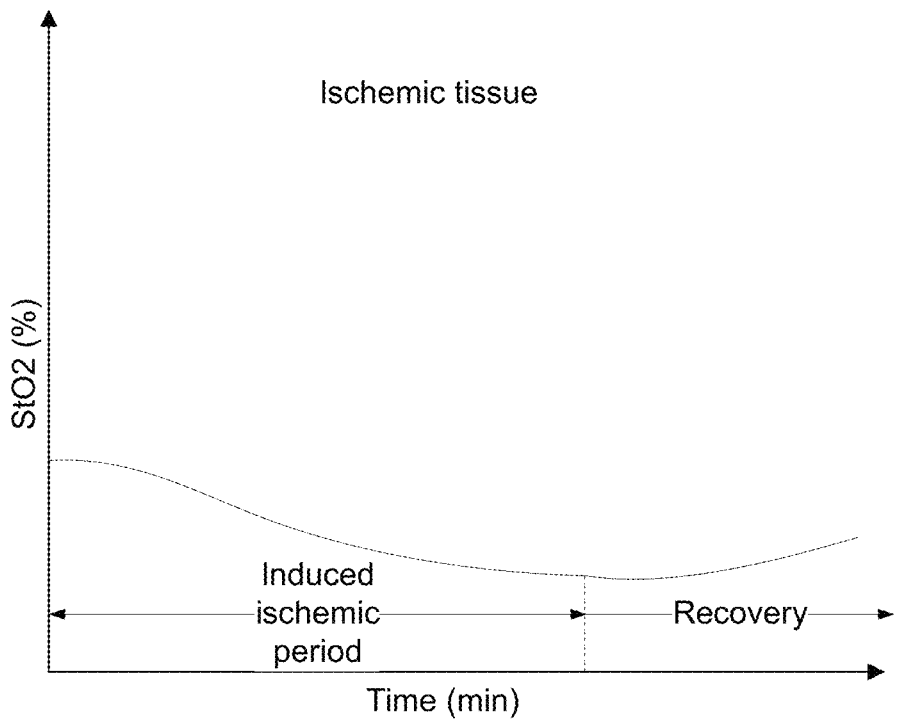
FIG. 16B shows a graph that shows oxygen saturation changes of an intestinal or mesentery tissue that is already ischemic during an induced ischemic period and during recovery.

In another aspect of the invention, a recovery pattern from a temporary induced ischemia of an intestinal or mesentery tissue can be analyzed to determine if a patient is suffering from intestinal ischemia. FIGS. 16A and 16B illustrate patterns of recovery from an induced ischemia for an intestinal or mesentery tissue. In other words, a recovery period shows how oxygen saturation of the tissue increases after a blood flow to the mesenteric artery is restored by either removing a clip or releasing the pressure applied to the mesenteric artery. FIG. 16A shows a recovery pattern for a healthy tissue where the tissue oxygen saturation is restored to the initial value at a relatively fast rate. By contrast, FIG. 16B shows a recovery pattern for a tissue which already suffers from intestinal ischemia. In FIG. 16B, the tissue oxygen saturation is restored to the initial value at a relatively slow rate.

Figure 17:
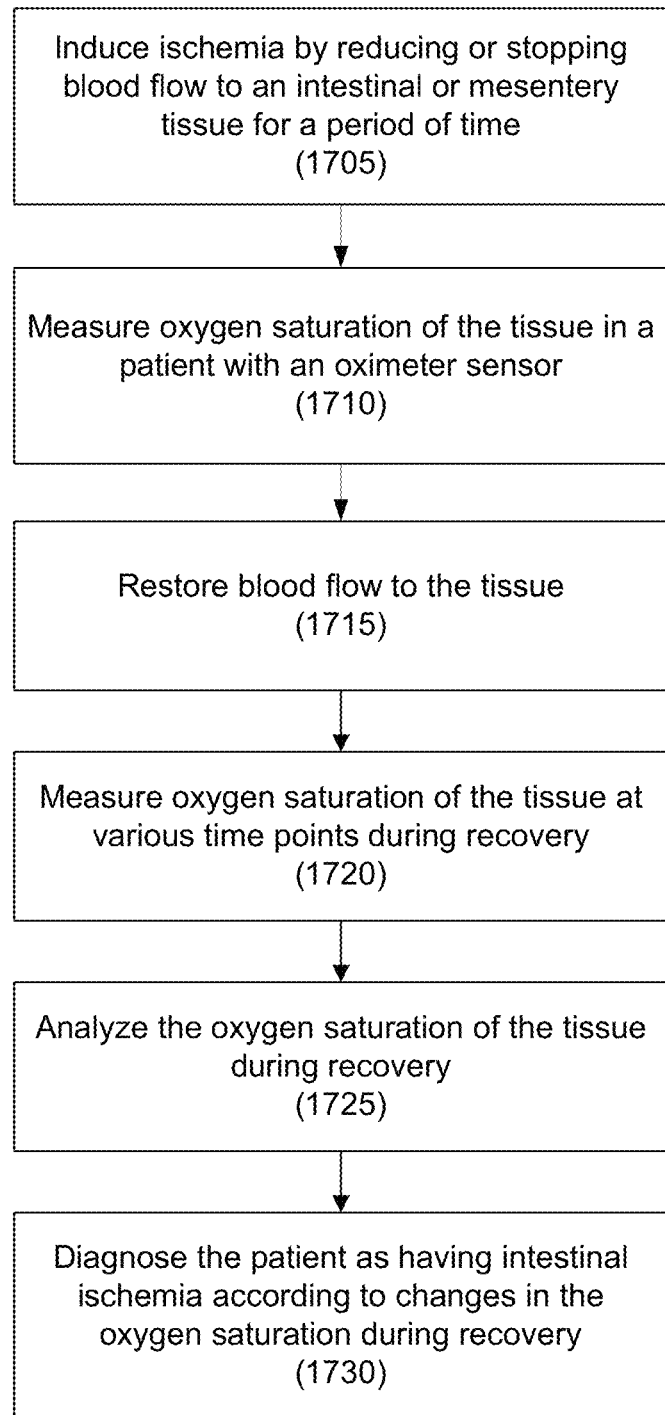
FIG. 17 shows a flow diagram for analyzing oxygen saturation changes of an intestinal or mesentery tissue during recovery phase from an induced ischemia to determine if a patient is suffering from intestinal ischemia.

FIG. 17 shows a flow diagram for diagnosing an intestinal ischemia in a patient by analyzing changes in oxygen saturation of an intestinal or mesentery tissue in a patient during recovery after a temporarily induced ischemic period.

In a step 1705, an ischemia is induced in the intestinal or mesentery tissue by reducing or stopping the blood flow (e.g., by clipping or pressing down the mesenteric artery) to the tissue.

In a step 1710, oxygen saturation of an intestinal or mesentery tissue in a patient is measured with an oximeter sensor.

In a step 1715, the blood flow to the tissue is restored (e.g., by removing pressure or clip on the mesenteric artery).

In a step 1720, oxygen saturation of the same portion of the tissue is remeasured with an oximeter sensor during recovery after the blood flow to the tissue is restored.

In a step 1725, the changes in tissue oxygen saturation during recovery are analyzed.

In a step 1730, the patient can be diagnosed as suffering from intestinal ischemia if changes in tissue oxygen saturation during recovery do not meet a threshold.

In one embodiment, the analysis in step 1725 may include calculating a rate of change of oxygen saturation over a period of time during recovery. For example, after the blood supply to the tissue is restored (e.g., by removing a clip), oxygen saturation of the tissue can be measured every 10 seconds, 30 seconds, one minute, two minutes, or other suitable time intervals. The measured oxygen saturation (e.g., in terms of percent) can be plotted against time. The rate of change can be calculated using any suitable method. For example, the rate of change can be measured and calculated around a midpoint of recovery phase (e.g., see FIG. 16A).

The rate of oxygen saturation change can be calculated, and compared to a threshold to determine whether the patient is suffering from intestinal or mesentery ischemia. A threshold can be set differently depending on various factors as noted above. A threshold can be set at any suitable rate, e.g., at about 3, 5, 10, 20, 30, 40, 50, 60, 70, 80, 90, 100, or 200 percent oxygen saturation per minute. For example, if the threshold is set at a rate of 50 percent oxygen saturation change per minute and if the patient's rate of change is calculated to be about 100 percent oxygen saturation change per minute, then the patient is diagnosed as not suffering from intestinal ischemia.

In another embodiment, the analysis in step 1725 may include determining an amount of time required for 80 percent recovery of oxygen saturation for the tissue after restoring the blood supply to the tissue. For a healthy, normal tissue, it typically takes less time to achieve 80 percent recovery of oxygen saturation for the tissue. By contrast, for a tissue which is suffering from intestinal ischemia, it typically takes longer time to achieve 80 percent recovery of oxygen saturation for the tissue.

The processes shown in FIGS. 12, 13, 15 and 17 are useful in diagnosing intestinal ischemia in a patient, as well as in monitoring and marking a tissue with a poor oxygen saturation level in the intestine or mesentery. Since embodiments of the invention can directly assess the oxygenation state of a full thickness of the intestine, they provide a better diagnostic tool in determining an ischemic condition of the intestine or mesentery at an earlier stage. Early diagnosis of intestinal ischemia is a key to successfully treating the disease. Embodiments of the invention contribute, among other things, in solving the problems related to a diagnosis of intestinal ischemia, locating ischemic tissue portions, as well as improving oxygen saturation measurements of the intestinal or mesentery tissue.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
during a recovery from a temporary ischemic period, contacting a serosal surface of a serosal tissue with a sensor probe comprising a first optical fiber;
transmitting radiation from a second optical fiber to the first optical fiber;
emitting the radiation from the first optical fiber into the contacted serosal surface of the serosal tissue;
collecting reflected radiation from the contacted serosal surface of the serosal tissue using the first optical fiber;
transmitting the reflected radiation from the first optical fiber to a third optical fiber;
measuring oxygen saturation of the serosal tissue during the recovery from a temporary ischemic period, after removing a constriction to a mesenteric artery, based on the radiation received in the third optical fiber;
analyzing the oxygen saturation of the serosal tissue of the intestinal or mesentery tissue during recovery from the temporary ischemic period; and
making a diagnosis of intestinal ischemia according to changes in the oxygen saturation in the serosal tissue of the intestinal or mesentery tissue during the recovery from the temporary ischemic period.

2. The method of claim 1 comprising:
inducing the temporary ischemic period for the serosal tissue of the intestinal or mesentery tissue by constricting the mesenteric artery that supplies blood to the serosal tissue of the intestinal or mesentery tissue; and
removing the constriction of the mesenteric artery that supplies blood to the serosal tissue of the intestinal or mesentery tissue to induce the recovery from the temporary ischemic period.

3. The method of claim 1 wherein the temporary ischemic period is induced by clipping or adding pressure on the mesenteric artery.

4. The method of claim 1 wherein the analyzing the oxygen saturation of the tissue comprises calculating a rate of change of the oxygen saturation during the recovery.

5. The method of claim 4 wherein the diagnosis of intestinal ischemia is made when the rate of change of the oxygen saturation is less than a threshold.

6. The method of claim 1 wherein the analyzing the oxygen saturation comprises calculating a time for the oxygen saturation to recover a specified percentage during the recovery.

7. The method of claim 1 wherein the serosal tissue comprises intestinal tissue.

8. The method of claim 1 wherein the serosal tissue comprises mesentery tissue.

9. A method comprising:
puncturing an outer tissue with a needle sensor device comprising a hollow needle and a sensor probe, the sensor probe comprising one or more optical fibers wherein distal ends of the one or more optical fibers are located at a tip of the sensor probe forming an oximeter sensor;
during a recovery from a temporary ischemic period, contacting a serosal surface of a serosal tissue with the tip of the sensor probe;
transmitting a first light, having a wavelength between about 600 nanometers to about 900 nanometers, into the serosal tissue through the one or more optical fibers at the tip of the sensor probe;
receiving a second light reflected from the serosal tissue through the one or more optical fibers at the tip of the sensor probe;
determining an oxygen saturation value for the serosal tissue based on values for the first and second light; and
making a diagnosis of intestinal ischemia according to changes in the oxygen saturation in the serosal tissue during the recovery from the temporary ischemic period.

10. A system for diagnosing an intestinal ischemia comprising:
a device to induce a temporary ischemic period in serosal tissue of an intestinal or mesentery tissue by constricting a mesenteric artery that supplies blood to the intestinal or mesentery tissue through an opening in outer tissue of an abdominal cavity;

a sensor probe comprising a first optical fiber, a second optical fiber, a third optical fiber, and a separating bar, wherein the first optical fiber has a first end and a second end, a hole is formed in the first end of the first optical fiber, the separating bar is positioned in the hole and extends from the first end of the first optical fiber, the second and third optical fibers are optically coupled to the first end of the first optical fiber, the separating bar is positioned between the second and third optical fibers at the first end of the first optical fiber, the second optical fiber is adapted to deliver a first radiation signal to the first optical fiber at the first end, the second end of the first optical fiber is adapted to contact the serosal tissue of the intestinal or mesentery tissue during the temporary ischemic period of the serosal tissue for emitting the first radiation signal into the serosal tissue and to detect a first reflected radiation signal reflected from the serosal tissue, the third optical fiber is adapted to receive the first reflected radiation signal from the first end of the first optical fiber, and based on the first reflected radiation signal received in the third optical fiber from the first optical fiber, the sensor probe measures oxygen saturation of the intestinal or mesentery tissue during recovery from the temporary ischemic period; and a system unit, coupled to the sensor probe, wherein the system unit is adapted to control the first and second optical fibers to transmit the first radiation signal and a second radiation signal to the serosal tissue, determine that a quality of a second reflected signal from the second radiation signal, which is transmitted from the first optical fiber to the third optical fiber, is within a first range, initiate transmission of the first radiation signal based on the quality of the second reflected signal being in the first range, and analyze the oxygen saturation in the serosal tissue of the intestinal or mesentery tissue during the recovery and makes a diagnosis of intestinal ischemia according to the oxygen saturation in the intestinal or mesentery tissue during the recovery.

11. The system of claim 10 wherein the sensor probe comprises a marking needle comprising a tip to mark the serosal tissue of the intestinal or the mesentery tissue after a measurement has been made.

12. The system of claim 10 wherein the first radiation signal comprises a wavelength of at least 690 nanometers.

13. The system of claim 10 wherein the first radiation signal comprises a wavelength of at least 830 nanometers.

14. The system of claim 10 wherein the first and second optical fibers are positioned on a surface of the sensor probe, separated by a distance of about 2 millimeters or less.

15. A system comprising:
a device to induce a temporary ischemic period in serosal tissue of an intestinal or mesentery tissue by constricting a mesenteric artery that supplies blood to the serosal tissue of the intestinal or mesentery tissue through an opening in outer tissue of an abdominal cavity;
a sensor probe comprising a first optical fiber, a second optical fiber, and a third optical fiber, wherein the first optical fiber is adapted to deliver radiation to the second optical fiber, the second optical fiber is adapted to contact the serosal tissue of the intestinal or mesentery tissue during the temporary ischemic period of the serosal tissue for emitting the radiation into the contacted serosal tissue and to detect reflected radiation reflected from the contacted serosal tissue, the third optical fiber is adapted to receive the reflected radiation from the second optical fiber, and based on the reflected radiation received in the third optical fiber from the second optical fiber, measure oxygen saturation of the serosal tissue of the intestinal or mesentery tissue during the temporary ischemic period of the serosal tissue; and a system unit, coupled to the sensor probe, which analyzes the oxygen saturation in the serosal tissue of the intestinal or mesentery tissue during the temporary ischemic period and makes a diagnosis of intestinal ischemia according to the oxygen saturation in the intestinal or mesentery tissue during the temporary ischemic period.

16. The system of claim 15 comprising:
a signal emitter circuit in the system unit, configured to send a first radiation signal through the second optical fiber of the sensor probe and a signal detector circuit is configured to receive the first reflected signal from the third optical fiber of the sensor probe,
wherein the first radiation signal emitted is light having a wavelength between about 600 nanometers to about 900 nanometers.

17. The system of claim 15 wherein a first radiation signal comprises a wavelength of at least 690 nanometers.

18. The system of claim 15 wherein a first radiation signal comprises a wavelength of at least 830 nanometers.

19. The system of claim 15 wherein the first and second optical fibers are positioned on a surface of the sensor probe, separated by a distance of about 2 millimeters or less.

20. The system of claim 15 wherein the system unit comprises an electronic processor.

21. A system comprising:
a device to induce a temporary ischemic period in serosal tissue of an intestinal or mesentery tissue by constricting a mesenteric artery that supplies blood to the serosal tissue of the intestinal or mesentery tissue through an opening in outer tissue of an abdominal cavity;
a sensor probe comprising a one or more optical fibers, wherein the one or more optical fibers is adapted to deliver radiation to the serosal tissue of the intestinal or mesentery tissue during the temporary ischemic period of the serosal tissue, the one or more optical fibers is adapted to receive the reflected radiation from the serosal tissue, and based on the reflected radiation received, measure oxygen saturation of the serosal tissue of the intestinal or mesentery tissue during the temporary ischemic period of the serosal tissue, and
the sensor probe is part of a needle sensor assembly comprising:
a hollow needle; and
distal ends of the one or more optical fibers are located at a tip of the sensor probe forming an oximeter sensor,
where the sensor probe is disposed inside the hollow needle and is configured to slide in and out of the hollow needle; and
a system unit, coupled to the sensor probe, which analyzes the oxygen saturation in the serosal tissue of the intestinal or mesentery tissue during the temporary ischemic period and makes a diagnosis of intestinal ischemia according to the oxygen saturation in the intestinal or mesentery tissue during the temporary ischemic period.

22. The system of claim 21 wherein the hollow needle comprises stainless steel.

\* \* \* \* \*